United States Patent
Nogueira et al.

(10) Patent No.: US 10,152,049 B2
(45) Date of Patent: Dec. 11, 2018

(54) GLUCOSE SENSOR HEALTH MONITORING AND RELATED METHODS AND SYSTEMS

(71) Applicant: MEDTRONIC MINIMED, INC., Northridge, CA (US)

(72) Inventors: Keith Nogueira, Mission Hills, CA (US); Xiaolong Li, Porter Ranch, CA (US); Rajiv Shah, Rancho Palos Verdes, CA (US); Brian T. Kannard, Mountain View, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 746 days.

(21) Appl. No.: 14/281,773

(22) Filed: May 19, 2014

(65) Prior Publication Data

US 2015/0331419 A1    Nov. 19, 2015

(51) Int. Cl.
  *G05B 23/00*    (2006.01)
  *A61M 5/172*    (2006.01)
  *A61M 5/142*    (2006.01)

(52) U.S. Cl.
  CPC ......... *G05B 23/00* (2013.01); *A61M 5/14244* (2013.01); *A61M 5/1723* (2013.01); *A61M 2205/70* (2013.01); *A61M 2205/702* (2013.01); *A61M 2230/201* (2013.01)

(58) Field of Classification Search
  CPC ............ A61M 5/1723; A61M 5/14244; A61M 2205/70; A61M 2230/201; G05B 23/00
  See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

Thomann et al., "An efficient monitoring concept with control charts for on-line sensors", 2002, Water Science and Technology vol. 46 No. 4-5 pp. 107-116.*

(Continued)

*Primary Examiner* — Regis Betsch
(74) *Attorney, Agent, or Firm* — Lorenz & Kopf, LLP

(57) ABSTRACT

Infusion systems, infusion devices, and related operating methods are provided. An exemplary method of operating an infusion device capable of delivering fluid to a user involves determining one or more signal characteristics associated with a subset of the measurements corresponding to a monitoring period, determining a reliability metric for the monitoring period based on the one or more signal characteristics, and providing indication of a maintenance condition when the reliability metric violates a threshold.

19 Claims, 15 Drawing Sheets

(56) References Cited

U.S. PATENT DOCUMENTS

| | | | |
|---|---|---|---|
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A * | 3/1996 | Schulman ......... A61B 5/14865 |
| | | 600/347 |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 * | 1/2001 | Say ................. A61B 5/14532 |
| | | 128/903 |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Llamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Llamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Llamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,474,332 B2 | 7/2013 | Bente, IV |
| 8,674,288 B2 | 3/2014 | Hanson et al. |
| 8,777,853 B2 * | 7/2014 | Kamath ............. A61B 5/14532 600/365 |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0004682 A1 * | 1/2009 | Kitamura ............ G01N 21/3577 435/14 |
| 2009/0081951 A1 | 3/2009 | Erdmann et al. |
| 2009/0082635 A1 | 3/2009 | Baldus et al. |
| 2010/0057042 A1 * | 3/2010 | Hayter ............... A61M 5/1723 604/504 |
| 2010/0057044 A1 * | 3/2010 | Hayter .............. A61M 5/14244 604/504 |
| 2011/0233393 A1 | 9/2011 | Hanson et al. |
| 2012/0108932 A1 * | 5/2012 | Roy ................... A61B 5/14532 600/365 |
| 2012/0108933 A1 | 5/2012 | Liang et al. |
| 2014/0039383 A1 * | 2/2014 | Dobbles .............. A61M 15/008 604/66 |
| 2014/0066889 A1 | 3/2014 | Grosman et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS

Marmarelis et al., "Data-driven Modeling for Diabetes: Diagnosis and Treatment". Mar. 2014, Springer p. 42, p. 78.*

PCT Search Report (PCT/US02/03299), Oct. 31, 2002, Medtronic Minimed, Inc.

(Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

(56) References Cited

OTHER PUBLICATIONS

Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-Tron® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/fag_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.

Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jonsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.

(56) References Cited

OTHER PUBLICATIONS

Nishida, Kenro, et al., "Clinical applications of teh wearable artificial endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

GLUCOSE SENSOR HEALTH MONITORING AND RELATED METHODS AND SYSTEMS

CROSS-REFERENCE TO RELATED APPLICATIONS

The subject matter described herein is also related to the subject matter described in U.S. patent application Ser. No. 14/281,770 and U.S. patent application Ser. No. 14/281,766, both filed concurrently herewith and incorporated by reference in their entirety.

TECHNICAL FIELD

Embodiments of the subject matter described herein relate generally to medical devices, and more particularly, embodiments of the subject matter relate to controlling operations of a portable electronic device, such as a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Rather than continuously sampling and monitoring a user's blood glucose level, which may compromise battery life, intermittently sensed glucose data samples may be utilized for determining operating commands for the infusion pump. To achieve the desired level of accuracy and reliability and reduce the impact of noise and other spurious signals, the sensor data is filtered and calibrated using a known good blood glucose value (e.g., a fingerstick measurement). However, the filtering introduces the appearance of lag, which can degrade the user experience. Additionally, various factors can lead to transient changes in the sensor output, which may influence the accuracy of the calibration. Degradation of sensor performance over time may further compound these problems. Accordingly, it is desirable to improve accuracy and reliability while also reducing lag and improving the overall user experience.

BRIEF SUMMARY

An embodiment of a method is provided for operating an infusion device to deliver fluid to a user based on measurements indicative of a physiological condition of the user provided by a sensing arrangement. An exemplary method involves determining one or more signal characteristics associated with a subset of the measurements corresponding to a monitoring period, determining a reliability metric for the monitoring period based on the one or more signal characteristics, and providing indication of a maintenance condition when the reliability metric violates a threshold.

In one embodiment, an infusion system is provided. The infusion system comprises a sensing element providing output signals influenced by a physiological condition in a body of a user and a control module coupled to the sensing element. The control module determines filtered measurements based on the output signals, determines one or more signal characteristics associated with a subset of the filtered measurements corresponding to a monitoring period, determines a reliability metric for the monitoring period based on the one or more signal characteristics, and provides indication of a maintenance condition for the sensing element when the reliability metric violates a threshold.

In another embodiment, a method of operating an infusion device operable to deliver insulin to a body of a user involves determining filtered measurements indicative of a glucose level in the body of the user based on output signals from a sensing element influenced by the glucose level in the body, determining one or more signal characteristics associated with a subset of the filtered measurements that correspond to a monitoring period, determining a reliability metric for the monitoring period based on the one or more signal characteristics, and providing a user notification to replace the sensing element when the reliability metric violates a threshold.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
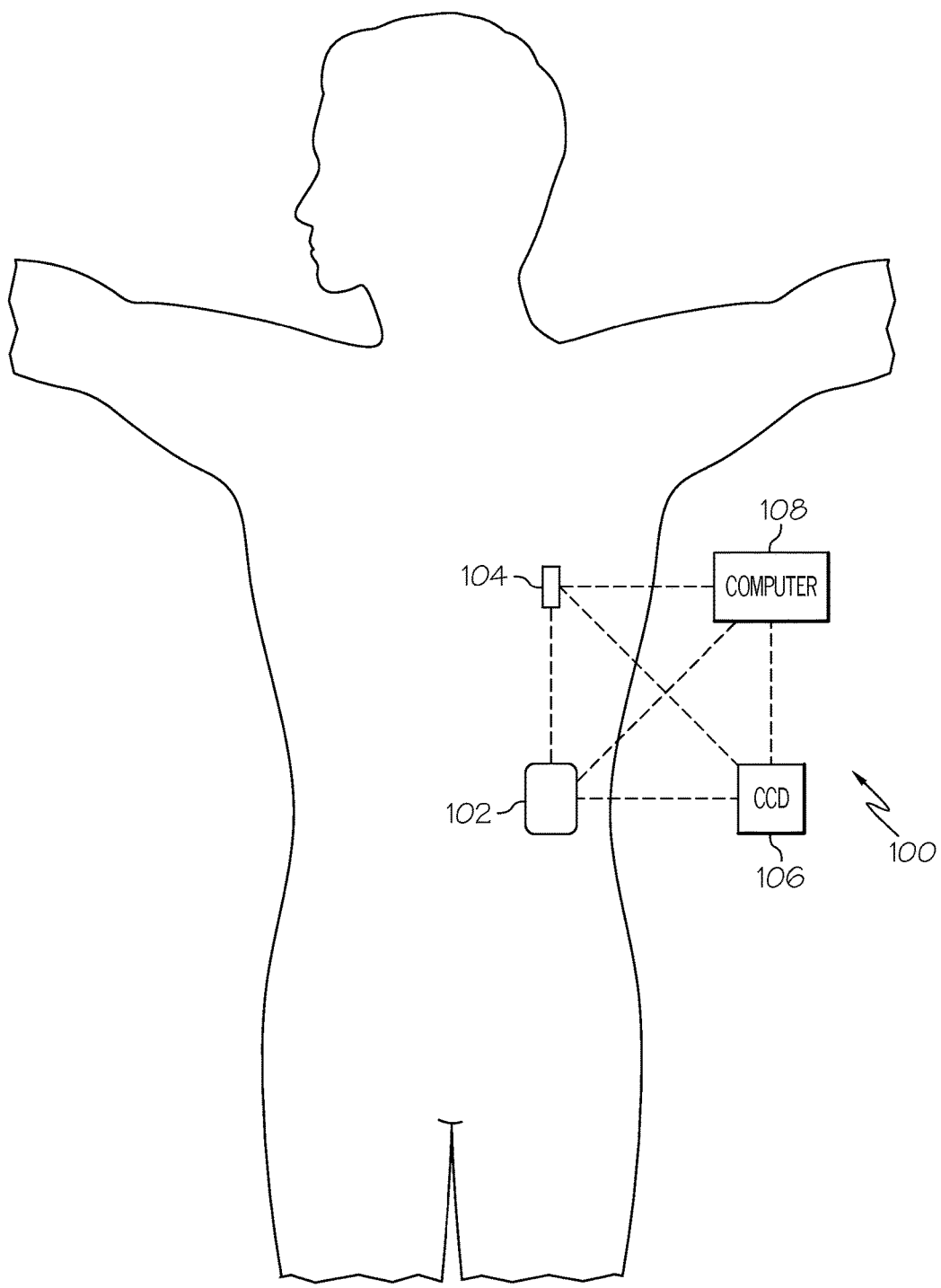
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein may be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097, 122; 6,485,465; 6,554,798; 6,558,320; 6,558,351; 6,641, 533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. As described in greater detail below, in exemplary embodiments, the dosage commands that govern operation of the motor are influenced by a current (or most recent) measurement of a condition in the body of the user. For example, in one or more embodiments, an insulin dosage (or delivery) command may be determined based on a difference between a current glucose measurement obtained for the user and a target glucose value for the user, where the current glucose measurement is determined based at least in part on one or more output signals obtained from a sensing element configured to sense, measure, or otherwise detect the relative amount of glucose present in the user's body. While the subject matter may be described herein in the context of delivering insulin to regulate a glucose level in the body of a user for purposes of explanation, it will be appreciated that the subject matter described herein it not limited to any particular type of fluid being delivered or any particular physiological condition being regulated.

As described in greater detail below in the context of FIGS. 6-11, in exemplary embodiments, the output signals from a sensing element sensitive to a user's glucose level are filtered to obtain filtered measurements indicative of the user's glucose level. The filtered measurements are analyzed to determine metrics indicative of signal characteristics of the filtered measurement signal based at least in part on one or more derivative metrics associated with the filtered measurements. For example, a first derivative metric associated with a respective filtered measurement may be calculated and utilized to determine a frequency metric indicative of an estimated frequency of the filtered measurement signal, while a second derivative metric may be calculated and utilized to determine a noise metric indicative of an estimate of the amount of noise present in the filtered measurement signal. A respective filtered measurement is adaptively filtered in a manner that is influenced by its associated frequency and noise metrics to obtain an uncalibrated measurement indicative of the user's glucose level that may be output or otherwise provided to another component of an infusion system, which, in turn, converts the uncalibrated output measurement into a calibrated sensor glucose value (or sensed glucose value) using a calibration factor associated with the sensing element. The sensed glucose value may be utilized in determining a delivery command, which, in turn, is utilized to operate a motor of the infusion device to deliver insulin to the body of the user.

In one or more embodiments, the calibration factor used to convert the uncalibrated output measurement determined by filtering output signals from the sensing element into a calibrated sensor glucose value is adjusted in a manner that is influenced by an expected calibration factor, as described in greater detail below in the context of FIGS. 12-14. A raw (or unadjusted) calibration factor may be determined based on the relationship between reference blood glucose measurements and corresponding uncalibrated output measurements that are paired with the respective reference blood glucose measurements. For example, in one embodiment, the raw calibration factor is determined as a ratio of a first weighted sum to a second weighted sum, where the first weighted sum is a sum of the products of the first weighted sum comprises a sum of products of the respective uncalibrated measurement and reference measurement of each respective pairing and one or more weighting factors associated with that respective pairing, while the second weighted sum comprises a sum of products of a square of the respective uncalibrated measurement and one or more weighting factors associated with its respective pairing. Thereafter, an expected calibration factor for the sensing element is utilized to determine an adjusted calibration factor based on the raw calibration factor. In this manner, the value of the adjusted calibration factor is adjusted from the value of the raw calibration factor towards the value of the expected calibration factor. For example, in one embodiment, the adjusted calibration factor is calculated as a weighted sum of the raw calibration factor and the expected calibration factor. In other embodiments, the adjusted calibration factor may be determined as a function of the raw calibration factor and an elapsed time since the most recent calibration attempt, where the function is configured to dynamically adjust the value of the adjusted calibration factor from the value of the raw calibration factor towards the expected calibration factor as the elapsed time increases.

As described in greater detail below in the context of FIG. 15, in exemplary embodiments, the filtered measurements based on the output signals from the sensing element are analyzed over a monitoring period to determine signal characteristics associated with the filtered measurement signal over the monitoring period. The signal characteristics associated with the filtered measurement signal over the monitoring period are, in turn, utilized to determine a reliability metric associated with the sensing element for the monitoring period. In exemplary embodiments, the reliability metric is indicative of the relationship between the noisiness of the filtered measurement signal and the magnitude of the filtered measurement signal. For example, in one embodiment, the reliability metric corresponds to a ratio of the average value of the filtered measurement signal over the monitoring period to a number of high noise measurements that occurred during that monitoring period. In this regard, the respective values of the subset of filtered measurements occurring during the monitoring period are averaged to obtain the average measurement value for the monitoring period. To determine the number of high noise measurements, a noise metric for each respective measurement of the subset of filtered measurements occurring during the monitoring period may be compared to a noise threshold to classify or otherwise identify that respective measurement as a high noise measurement when the value of noise metric exceeds the noise threshold value. Thereafter, the average measurement value for the monitoring period is divided by the number of high noise measurements to obtain a reliability metric indicative of the relationship between the magnitude and the noisiness of the filtered measurement signal.

When the reliability metric violates a maintenance threshold value, an indication of a maintenance condition may be generated or otherwise provided to a user. For example, an auditory and/or visual user notification may be automatically generated that indicates replacement of the sensing element should be performed, or alternatively, that some other maintenance of the sensing element should otherwise be performed (e.g., inspecting electrical connectivity to/from the sensing element, ensuring the sensing element is properly inserted and/or fitted in a housing of a sensing device, or the like). In one or more embodiments, the indication of a maintenance condition is automatically provided only when the reliability metric is less than the maintenance threshold value for at least a threshold number of consecutive monitoring periods. For example, in one embodiment, the monitoring periods have a duration of two hours, where a user notification is automatically generated when the reliability metric is less than the maintenance threshold value for at least three (or more than two) consecutive monitoring periods, or in other words, when the output from the sensing element indicates relatively low reliability over the course of at least six hours. Thus, in such embodiments, the reliability metric may fall below the maintenance threshold for a monitoring period (e.g., as a result of interference or some other transient condition) before recovering to values above maintenance threshold for subsequent monitoring periods without any user notifications being generated. As a result, the usable lifetime of the sensing element may be extended by avoiding prematurely indicating replacement.

Turning now to FIG. 1, one exemplary embodiment of an infusion system 100 includes, without limitation, a fluid infusion device (or infusion pump) 102, a sensing arrangement 104, a command control device (CCD) 106, and a computing device 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computing device 108. For example, the infusion device 102, the CCD 106 and/or the computing device 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computing device 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computing device 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computing device 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computing device 108 may include electronics and other components configured to perform processing, delivery routine storage, and to control the infusion device 102 in a manner that is influenced by sensor data measured by and/or received from the sensing arrangement 104. By including control functions in the CCD 106 and/or the computing device 108, the infusion device 102 may be made with more simplified electronics. However, in other embodiments, the infusion device 102 may include all control functions, and may operate without the CCD 106 and/or the computing device 108. In addition, the infusion device 102 and/or the sensing arrangement 104 may be configured to transmit data to the CCD 106 and/or the computing device 108 for display or processing of the data by the CCD 106 and/or the computing device 108. In various embodiments, the CCD 106 and/or the computing device 108 may be a portable electronic device, such as a mobile phone, a smartphone, a tablet computer, a notebook or laptop computer, or the like. In one embodiment, the computing device 108 is a server computer that is accessible via a communications network, such as the Internet, a cellular network, or the like.

In some embodiments, the CCD 106 and/or the computing device 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
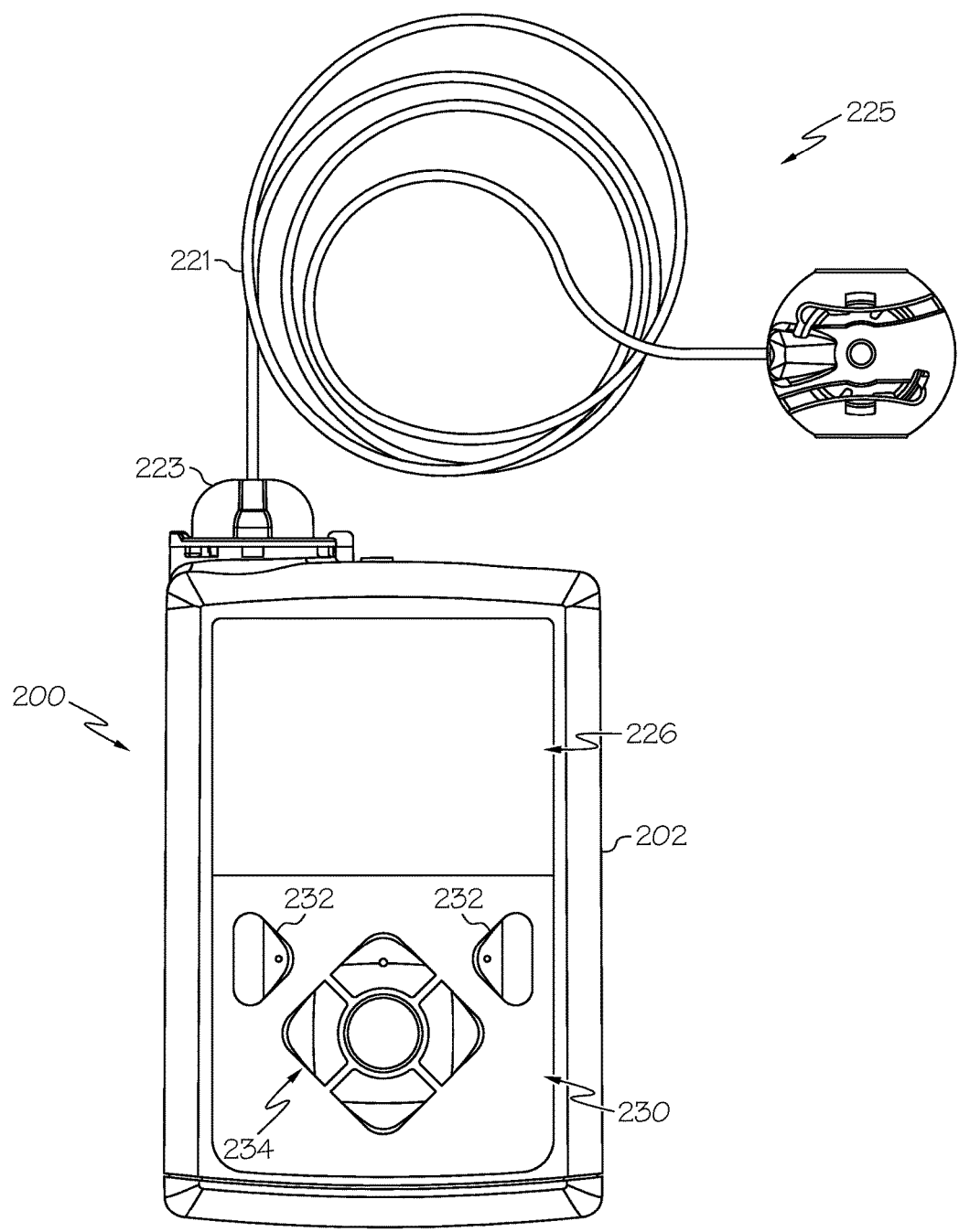
FIG. 2 depicts a plan view of an exemplary embodiment of a fluid infusion device suitable for use in the infusion system of FIG. 1.
Figure 3:
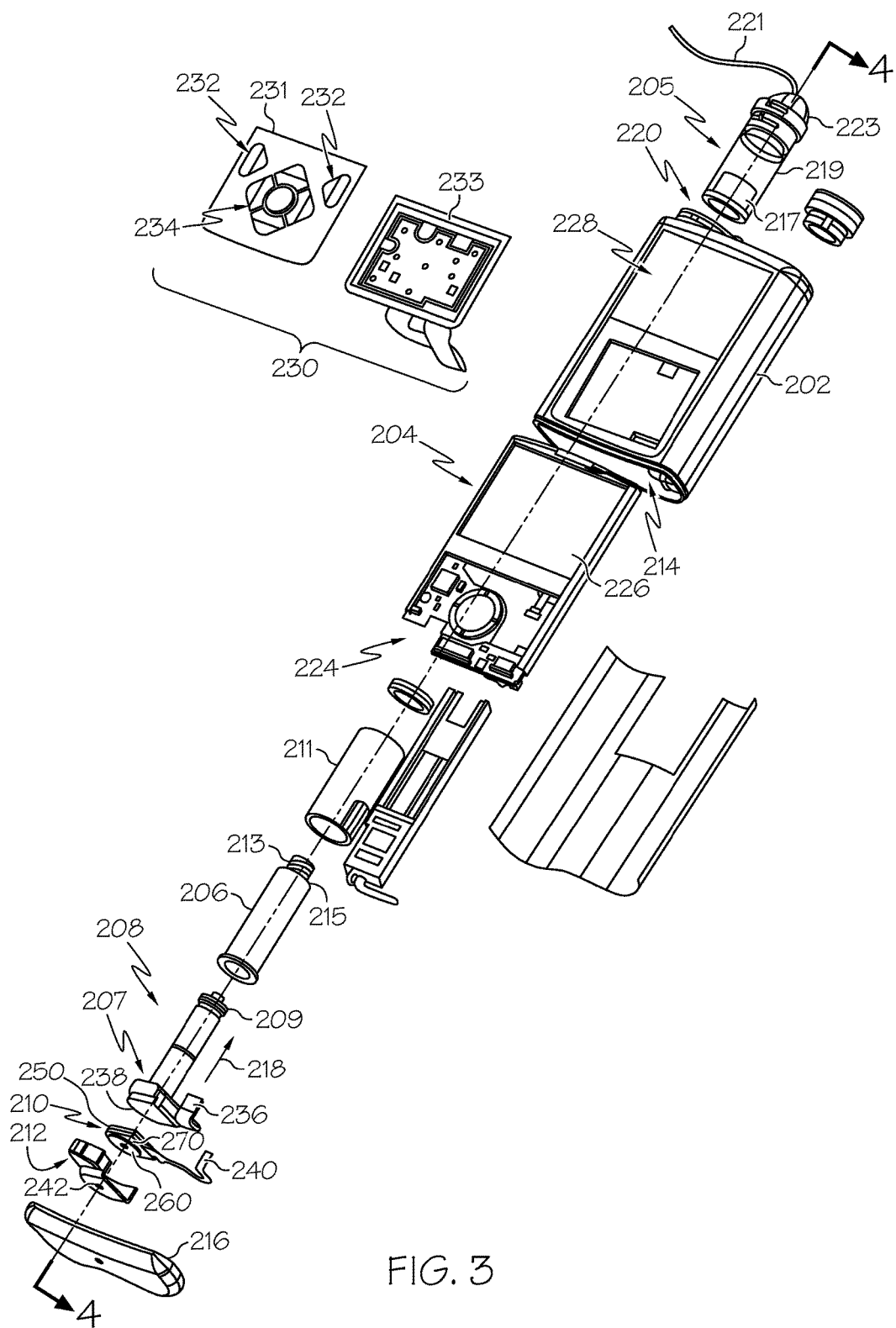
FIG. 3 is an exploded perspective view of the fluid infusion device of FIG. 2.
Figure 4:
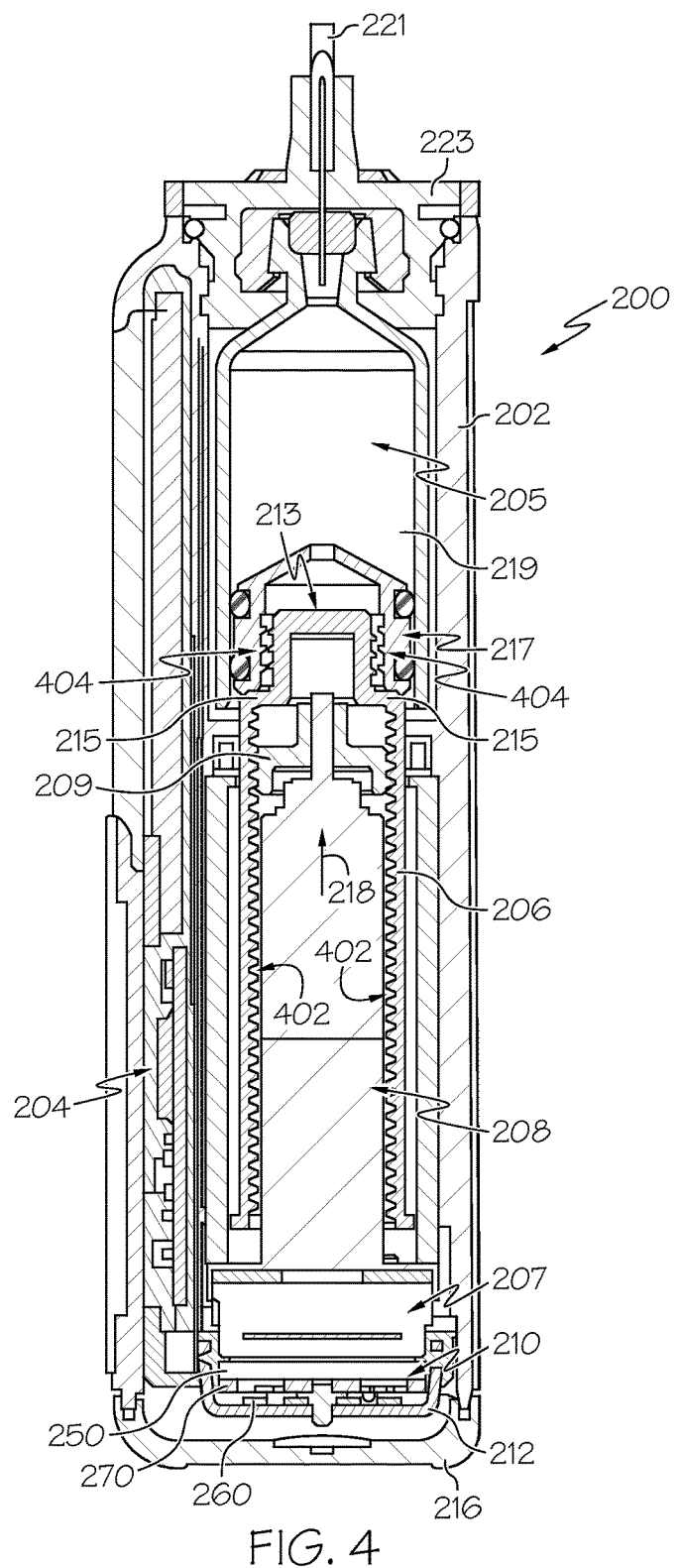
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. patent application Ser. No. 12/908,807, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
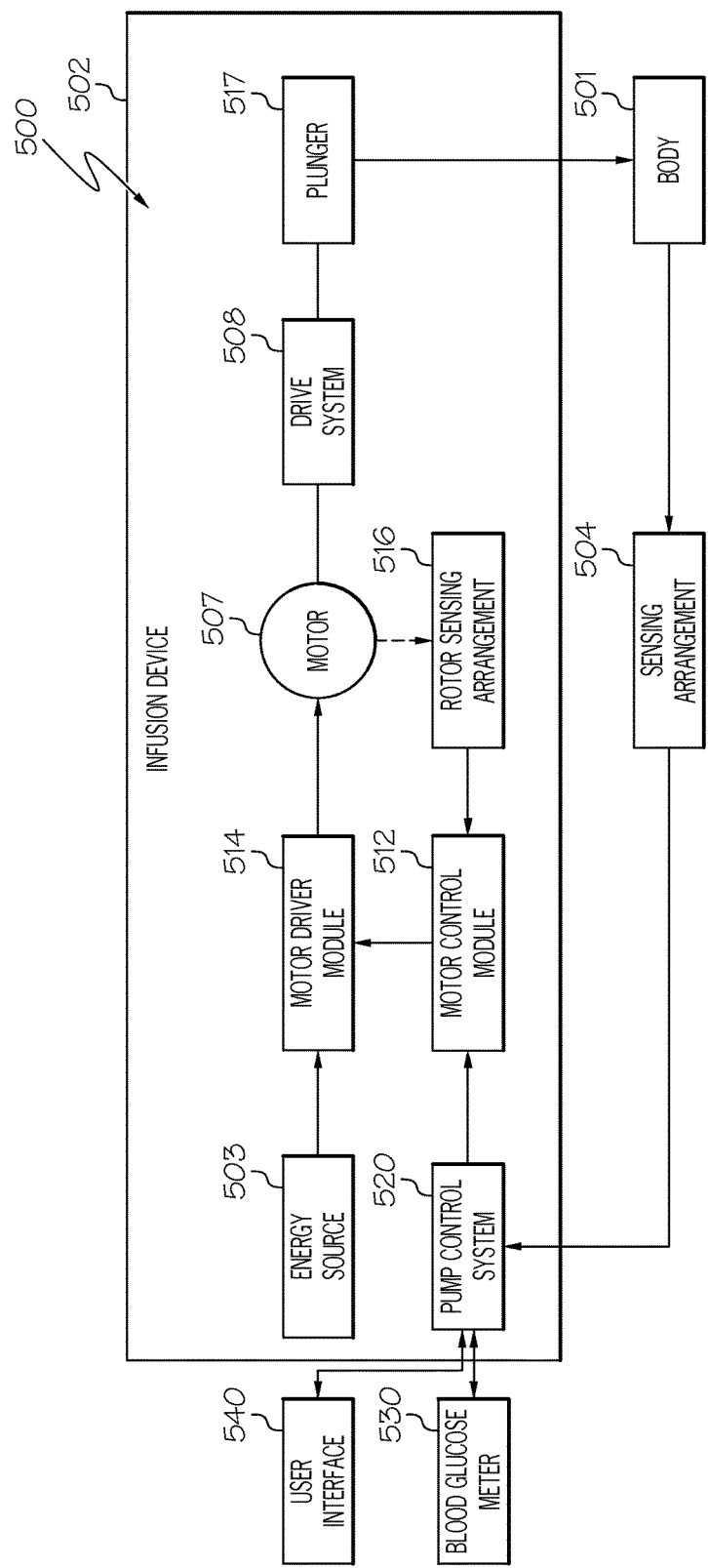
FIG. 5 is a block diagram of an exemplary control system suitable for use in a fluid infusion device, such as the fluid infusion device of FIG. 1.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a user to a desired (or target) value or otherwise maintain the condition within a range of acceptable values. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

As described in greater detail below in the context of FIG. 6, in exemplary embodiments, the sensing arrangement 504 includes one or more interstitial glucose sensing elements generate or otherwise output electrical signals having a signal characteristic that is correlative to, influenced by, or otherwise indicative of the relative interstitial fluid glucose level in the body 501 of the user. The output electrical signals are filtered or otherwise processed to obtain a filtered measurement value indicative of the user's interstitial fluid glucose level. In exemplary embodiments, the control system 500 includes a blood glucose meter 530, such as a finger stick device, which is configured to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting an uncalibrated filtered measurement value indicative of the user's interstitial fluid glucose level into a corresponding calibrated blood glucose value, as described in greater detail below. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of the current blood glucose level in the body 501 of the user. To support closed-loop control, the pump control system 520 maintains, receives, or otherwise obtains a desired value for a condition in the body 501 of the user to be regulated (e.g., a target or commanded glucose value), and generates or otherwise determines dosage commands for operating the motor 507 to displace the plunger 517 based at least in part on a difference between the sensed glucose value and the target glucose value. In practice, the infusion device 502 may store or otherwise maintain the target value in a data storage element accessible to the pump control system 520. The target value may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 508 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 508 may be integrated with the infusion device 502. Furthermore, in some embodiments, one or more user interface element(s) 540 are integrated with the sensing arrangement 504 in addition to and/or in alternative to the user interface element(s) 508 integrated with the infusion device 502.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108. Additionally, although FIG. 5 depicts the sensing arrangement 504 as being physically separate and distinct from the infusion device 502, in alternative embodiments, the sensing arrangement 504 may be integrated into or otherwise implemented by the infusion device 502 (e.g., by providing the sensing arrangement 504 within the housing 202). Furthermore, more complex control schemes may be implemented by the pump control system 520 with multiple sensing arrangements 504 being utilized in conjunction with one another.

Figure 6:
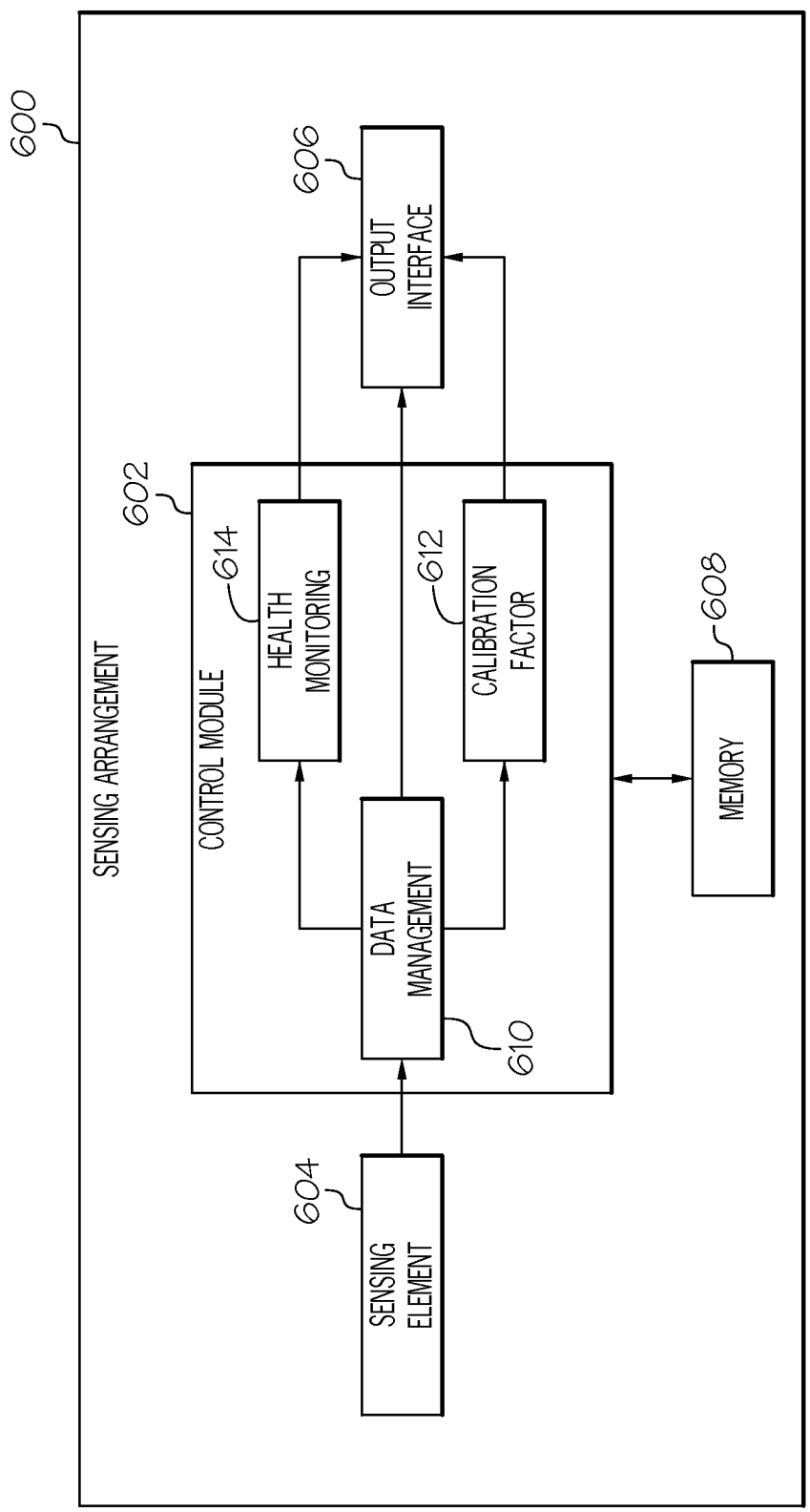
FIG. 6 is a block diagram of an exemplary electronic device suitable for use as the sensing arrangement in the control system of FIG. 5.

FIG. 6 depicts an exemplary embodiment of an electronic device 600 suitable for use as the sensing arrangement 504 of FIG. 5 in accordance with one or more embodiments. For purposes of explanation, but without limitation, the device 600 may alternatively be referred to herein as a sensing device or a sensing arrangement. The illustrated sensing device 600 includes, without limitation, a control module 602, a sensing element 604, an output interface 606, and a data storage element (or memory) 608. The control module 602 is coupled to the sensing element 604, the output interface 606, and the memory 608, and the control module 602 is suitably configured to support the operations, tasks, and/or processes described herein.

The sensing element 604 generally represents the component of the sensing device 600 that is configured to generate, produce, or otherwise output one or more electrical signals indicative of a condition that is sensed, measured, or otherwise quantified by the sensing device 600. In this regard, the physiological condition of a user influences a characteristic of the electrical signal output by the sensing element 604, such that the characteristic of the output signal corresponds to or is otherwise correlative to the physiological condition that the sensing element 604 is sensitive to. For example, referring to FIG. 5, the sensing element 604 may be realized as a glucose sensing element that generates an output electrical signal having a current (or voltage) associated therewith that is correlative to the interstitial fluid glucose level that is sensed or otherwise measured in the body 501 of the user by the sensing arrangement 504, 600.

Still referring to FIG. 6, the control module 602 generally represents the hardware, circuitry, logic, firmware and/or other component(s) of the sensing device 600 that is coupled to the sensing element 604 to receive the electrical signals output by the sensing element 604 and perform various additional tasks, operations, functions and/or processes described herein. For example, in one or more embodiments, the control module 602 implements or otherwise executes a data management application module 610 that filters, analyzes or otherwise processes the electrical signals received from the sensing element 604 to obtain a filtered measurement value indicative of the measured interstitial fluid glucose level, as described in greater detail below in the context of FIGS. 7-11. Additionally, in one or more embodiments, the control module 602 also implements or otherwise executes a calibration application module 612 that calculates or otherwise determines a calibration factor for converting the filtered measurement value from the data management application 610 to a sensed glucose value based at least in part on one or more filtered measurement values from the data management application 610 and corresponding reference blood glucose measurement values (e.g., from blood glucose meter 530) paired with those filtered measurement values, as described in greater detail below in the context of FIGS. 12-14. In some embodiments, the control module 602 also implements or otherwise executes a health monitoring application module 614 that detects or otherwise identifies replacement or other maintenance with respect to the sensing element 604 is desirable based on signal characteristics associated with the output electrical signals from the sensing element 604, as described in greater detail below in the context of FIG. 15.

Depending on the embodiment, the control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 602, or in any practical combination thereof.

In some embodiments, the control module 602 includes an analog-to-digital converter (ADC) or another similar sampling arrangement that samples or otherwise converts the output electrical signal received from the sensing element 604 into corresponding digital measurement data value. In other embodiments, the sensing element 604 may incorporate an ADC and output a digital measurement value. For purposes of explanation, the input to the data management application 610 from the sensing element 604 may alternatively be referred to herein as the unfiltered measurement value, which should be understood as referring to the digital value correlative to the interstitial fluid glucose level sensed by the sensing element 604. In one or more embodiments, the current of the electrical signal output by the sensing element 604 is influenced by the user's interstitial fluid glucose level, and the input to the data management application 610 is realized as an unfiltered current measurement value. As described above, depending on the embodiment, the unfiltered measurement value may be output directly by the sensing element 604 or converted based on an analog electrical output signal from the sensing element 604 by an ADC of the control module 602.

In exemplary embodiments, the control module 602 includes or otherwise accesses the data storage element or memory 608. The memory 608 may be realized using any sort of RAM, ROM, flash memory, registers, hard disks, removable disks, magnetic or optical mass storage, short or long term storage media, or any other non-transitory computer-readable medium capable of storing programming instructions, code, or other data for execution by the control module 602. The computer-executable programming instructions, when read and executed by the control module 602, cause the control module 602 to implement or otherwise generate the applications 610, 612, 614 and perform the tasks, operations, functions, and processes described in greater detail below.

The output interface 606 generally represents the hardware, circuitry, logic, firmware and/or other components of the sensing device 600 that are coupled to the control module 602 for outputting data and/or information from/to the sensing device 600 to/from the infusion device 502, the pump control system 520 and/or the user. In this regard, in exemplary embodiments, the output interface 606 is realized as a communications interface configured to support communications to/from the sensing device 600. In such embodiments, the communications interface 606 may include or otherwise be coupled to one or more transceiver modules capable of supporting wireless communications between the sensing device 600 and another electronic device (e.g., an infusion device 102, 502 or another electronic device 106, 108 in an infusion system 100). Alternatively, the communications interface 606 may be realized as a port that is adapted to receive or otherwise be coupled to a wireless adapter that includes one or more transceiver modules and/or other components that support the operations of the sensing device 600 described herein. In other embodiments, the communications interface 606 may be configured to support wired communications to/from the sensing device 600. In yet other embodiments, the output interface 606 may include or otherwise be realized as an output user interface element, such as a display element (e.g., a light-emitting diode or the like), a display device (e.g., a liquid crystal display or the like), a speaker or another audio output device, a haptic feedback device, or the like, for providing notifications or other information to the user. In such embodiments, the output user interface 606 may be integrated with the sensing arrangement 504, 600 (e.g., within a common housing) or implemented separately (e.g., user interface element 540).

It should be understood that FIG. 6 is a simplified representation of a sensing device 600 for purposes of explanation and is not intended to limit the subject matter described herein in any way. In this regard, although FIG. 6 depicts the various elements residing within the sensing device 600, one or more elements of the sensing device 600 may be distinct or otherwise separate from the other elements of the sensing device 600. For example, the sensing element 604 may be separate and/or physically distinct from the control module 602 and/or the communications interface 606. Furthermore, although FIG. 6 depicts the applications 610, 612, 614 as being implemented by the sensing device 600, in alternative embodiments, features and/or functionality of one or more of the applications 610, 612, 614 may be implemented by or otherwise reside on the infusion device 102, 502 or another device 106, 108 within an infusion system 100. For example, in some embodiments, the features and/or functionality of one or more of the applications 610, 612, 614 may be implemented by the pump control system 520.

Figure 7:
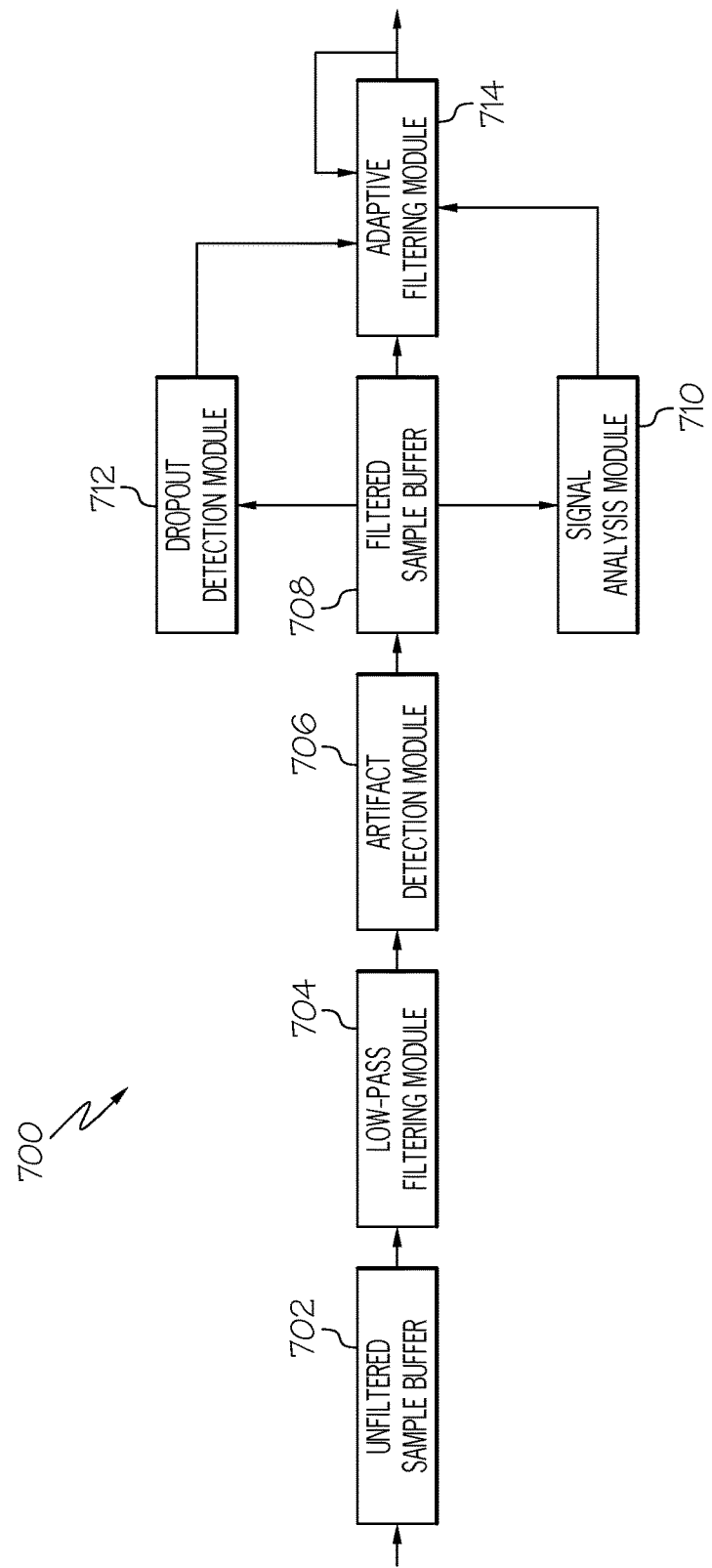
FIG. 7 is a block diagram of an exemplary signal processing system suitable for implementation by the data management application in the sensing arrangement of FIG. 6.

FIG. 7 depicts an exemplary embodiment of a signal processing system 700 suitable for implementation by the data management application 610 in the sensing arrangement 600 of FIG. 6 in accordance with one or more embodiments. The illustrated signal processing system 700 includes, without limitation, an unfiltered sample buffer 702, a first filtering module 704, an artifact detection module 706, a filtered sample buffer 708, a signal analysis module 710, a dropout detection module 712, and a second filtering module 714. It should be understood that FIG. 7 is a simplified representation of a signal processing system 700 for purposes of explanation and is not intended to limit the subject matter described herein in any way. In this regard, practical embodiments of the signal processing system 700 may include additional components and/or elements configured to perform additional signal processing features and/or functionality which are not described herein.

The unfiltered sample buffer 702 generally represents a data storage element (e.g., a particular allocated portion of memory 608) that is coupled to the sensing element 604 (e.g., via an ADC) and configured to store or otherwise maintain a plurality of unfiltered measurement values most recently obtained from the sensing element 604. In one or more exemplary embodiments, an unfiltered measurement value is obtained from the sensing element 604 on a per-minute basis (e.g., by periodically sampling the output of the sensing element 604 once every minute), with the unfiltered sample buffer 702 storing the 8 most recent unfiltered measurement values.

The first filtering module 704 accesses the unfiltered sample buffer 702 to obtain the most recent unfiltered measurement values and low-pass filters the unfiltered measurement values to obtain a filtered measurement value corresponding to the most recent sampling time. In exemplary embodiments, the low-pass filtering module 704 applies asymmetric finite impulse response (FIR) filter coefficients to the 8 most recent unfiltered measurement values to obtain a filtered measurement value corresponding to the most recent sampling time. In this regard, for samples obtained on a per-minute basis, the filter coefficients may be chosen to provide a group delay of about one minute or less. In other words, the group delay is less than the sampling period. In exemplary embodiments, the low-pass filtering module 704 obtains the unfiltered measurement values from the unfiltered sample buffer 702 on a periodic basis at a frequency that is less than or equal to the rate at which the unfiltered sample buffer 702 is updated. For example, the unfiltered sample buffer 702 may be updated once every minute while the low-pass filtering module 704 filters the unfiltered measurement values once every five minutes. Accordingly, for purposes of explanation, a filtered measurement value output by the low-pass filtering module 704 may alternatively be referred to herein as a five-minute filtered measurement value.

The artifact detection module 706 is coupled to the output of the first filtering module 704 and analyzes the filtered measurement value to determine whether or not the filtered measurement value is indicative of an artifact in one or more of the unfiltered measurement values before providing the filtered measurement value to the filtered sample buffer 708. In this regard, the artifact detection module 706 detects or otherwise identifies when the magnitude of the change in the five-minute filtered measurement value relative to the preceding five-minute filtered measurement value is unlikely to be exhibited in the body of a user, as described in greater detail below in the context of FIG. 8. In this regard, the filtered sample buffer 708 also maintains, in association with each respective five-minute filtered measurement value, an indication of whether or not that filtered measurement value is valid and usable by the second filtering module 714, the pump control system 520 and/or other components in the control system 500.

Additionally, the artifact detection module 706 may analyze the filtered measurement value to verify or otherwise confirm the filtered measurement value is within an acceptable range of values, and flag or otherwise mark any filtered measurement value outside of the acceptable range of values as being invalid or otherwise unusable.

In exemplary embodiments, the filtered sample buffer 708 stores or otherwise maintains a plurality of filtered measurement values. For example, in one or more embodiments, the filtered sample buffer 708 stores the eight most recent five-minute filtered measurement values. As described in greater detail below in the context of FIG. 9, the signal analysis module 710 accesses the filtered measurement values in the filtered sample buffer 708 and analyzes the filtered measurement values to calculate or otherwise identify one or more metrics indicative of signal characteristics associated with the five-minute filtered measurement signal. In exemplary embodiments, the signal analysis module 710 determines an estimate of the signal noise (or noise metric) associated with the filtered measurement values at the respective sampling time of a respective filtered measurement value along with an estimate of the signal frequency (or frequency metric) associated with the filtered measurement values. As described in greater detail below in the context of FIG. 11, the second filtering module 714 is coupled to the signal analysis module 710 to obtain the signal characteristic metrics determined by the signal analysis module 710 and adaptively filter the most recent five-minute filtered measurement value in the filtered sample buffer 708 based at least in part on the signal characteristic metrics. In one embodiment, the second filtering module 714 implements a Kalman filter that filters the filtered measurement value input to the adaptive filtering module 714 from the buffer 708 using the measurement value previously output by the adaptive filtering module 714 and the signal characteristic metrics from the signal analysis module 710. In exemplary embodiments, the adaptive filtering module 714 is also coupled to the dropout detection module 712, which is configured to detect or otherwise identify dropouts in the five-minute filtered measurement signal as described in greater detail below in the context of FIG. 10. In this regard, in response to detecting a dropout condition, the adaptive filtering module 714 is configured to adjust or otherwise modify the amount of filtering to account for the dropout condition.

Figure 8:
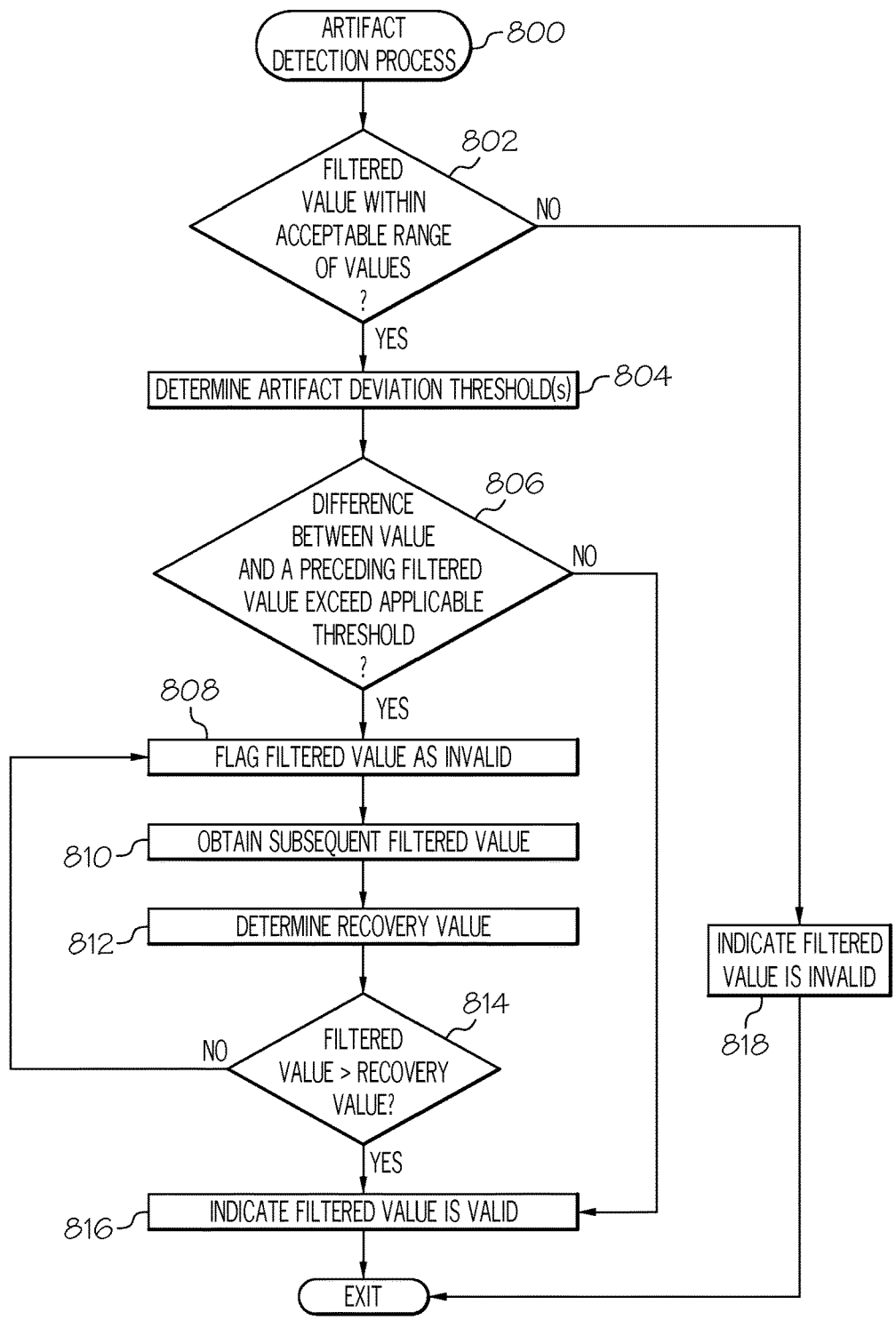
FIG. 8 is a flow diagram of an exemplary artifact detection process suitable for implementation by the artifact detection module in the signal processing system of FIG. 7.

FIG. 8 depicts an exemplary artifact detection process 800 suitable for implementation by the sensing arrangement 504, 600 to detect or otherwise identify invalid or otherwise unusable measurement values. The various tasks performed in connection with the artifact detection process 800 may be performed by hardware, firmware, software executed by processing circuitry, or any combination thereof. For illustrative purposes, the following description refers to elements mentioned above in connection with FIGS. 1-7. In practice, portions of the artifact detection process 800 may be performed by different elements of the sensing arrangement 504, 600 and/or control system 500. That said, in exemplary embodiments described herein, the artifact detection process 800 is performed by the artifact detection module 706 of the data management application 610 implemented by the control module 602. It should be appreciated that the artifact detection process 800 may include any number of additional or alternative tasks, the tasks need not be performed in the illustrated order and/or the tasks may be performed concurrently, and/or the artifact detection process 800 may be incorporated into a more comprehensive procedure or process having additional functionality not described in detail herein. Moreover, one or more of the tasks shown and described in the context of FIG. 8 could be omitted from a practical embodiment of the artifact detection process 800 as long as the intended overall functionality remains intact.

In exemplary embodiments, the artifact detection process 800 initializes or otherwise begins by receiving or otherwise obtaining a new filtered measurement value and verifying or otherwise confirming the filtered measurement value is not invalid (task 802). In this regard, the artifact detection process 800 receives a new filtered measurement value from the low-pass filtering module 704 and confirms that the filtered measurement value is within an acceptable range of values. For example, in one embodiment, the artifact detection process 800 confirms the filtered measurement value corresponds to a current through the sensing element 604 that is greater than a minimum acceptable threshold current threshold value and less than a maximum acceptable threshold current value. When it is determined that the filtered measurement value is not within the acceptable range of values, the artifact detection process 800 determines the filtered measurement value is invalid or otherwise should not be utilized for subsequent calculations and marks or otherwise indicates the filtered measurement value as being invalid (task 818). In this regard, when the artifact detection process 800 determines a five-minute filtered measurement value is not within the range of acceptable values, the artifact detection process 800 stores that five-minute filtered measurement value in the buffer 708 in association with an indicator or flag that designates the filtered measurement value is invalid or otherwise unusable.

When the filtered measurement value is otherwise acceptable, the illustrated process 800 continues by calculating or otherwise determining one or more artifact deviation thresholds and identifying whether a difference between the filtered measurement value and a respective preceding filtered measurement value is greater than an applicable artifact deviation threshold (tasks 804, 806). In this regard, an artifact deviation threshold represents a change in the filtered measurement value over a particular amount of time that is unlikely to be exhibited in the body 501 of the user and is most likely attributable to an artifact in the output signal generated by the sensing element 604. For example, in one embodiment, the artifact detection module 706 calculates the artifact deviation threshold between the instant filtered measurement value and the preceding filtered measurement value by multiplying the preceding measurement value by a percentage indicative of a change over the time difference between successive samples (e.g., 5 minutes) that is likely to be attributable to an artifact. Similarly, the artifact detection module 706 may calculate a ten minute artifact deviation threshold between the current filtered measurement value and the second preceding filtered measurement value (e.g., from two samples ago) by multiplying that preceding measurement value by a larger percentage indicative of a change between a larger time difference (e.g., 10 minutes) that is likely to be attributable to an artifact, and so on. In this manner, one or more of the artifact deviation threshold values may vary dynamically based on the magnitude(s) of one or more of the preceding filtered measurement values. In some embodiments, the artifact detection module 706 may also apply one or more fixed artifact deviation thresholds to the difference(s) between the current filtered measurement value and one or more preceding filtered measurement values. For example, the artifact detection module 706 may detect an artifact when the difference between the current filtered measurement value and the preceding filtered measurement value is greater than a first artifact deviation threshold current value, or when the difference between the current filtered measurement value and the second preceding filtered measurement value exceeds a greater artifact deviation threshold current value, and so on.

When the differences between the current filtered measurement value and the preceding filtered measurement value(s) are less than the applicable artifact deviation threshold(s), the artifact detection process 800 marks or otherwise indicates the current filtered measurement value is valid or otherwise usable for subsequent calculations (task 816). In this regard, the artifact detection module 706 may store the five-minute filtered measurement value in the buffer 708 in association with an indicator or flag that designates the filtered measurement value as being valid and usable. Conversely, in response to determining a difference between the current filtered measurement value and a particular preceding filtered measurement value exceeds the applicable artifact deviation value corresponding to the time difference between those two filtered measurement values, the artifact detection process 800 continues by marking or otherwise indicating the current filtered measurement value as being invalid (task 808). In a similar manner as described above, the artifact detection module 706 may store the filtered measurement value in the buffer 708 in association with an indicator or flag that designates the filtered measurement value is invalid or otherwise unusable. In some embodiments, the artifact detection process 800 may exit after marking the current filtered measurement value as invalid and reinitialize on the next subsequent filtered measurement value. For example, in one embodiment, when the difference between the current filtered measurement value and the preceding filtered measurement value is greater than first percentage of the preceding filtered measurement value but less than a larger percentage of the preceding filtered measurement value, the artifact detection process 800 may indicate the current filtered measurement value is invalid and exit.

In the illustrated embodiment, the artifact detection process 800 receives or otherwise obtains the next subsequent filtered measurement value, calculates or otherwise determines a recovery value based on the most recent valid filtered measurement value and the time elapsed since the most recent valid filtered measurement value, and verifies or otherwise confirms that subsequently filtered measurement value is greater than the recovery value (tasks 810, 812, 814). In this regard, the artifact detection process 800 may persistently mark subsequent filtered measurement values as invalid until a filtered measurement value indicates the filtered measurement signal has recovered from the artifact condition (task 808). In some embodiments, the recovery value dynamically decreases as the amount of time elapsed since detecting the artifact condition increases. For example, for the first sample immediately following detection of an artifact, the artifact detection module 706 may calculate or otherwise determine the recovery value is equal to 75% of the most recent valid filtered measurement value. If that filtered measurement value is greater than 75% of the most recent valid filtered measurement value, the artifact detection module 706 stores that filtered measurement value in the buffer 708 in association with an indication that that filtered measurement value is valid. Otherwise, the artifact detection module 706 stores that filtered measurement value in the buffer 708 in association with an indicator or flag that designates it as being invalid. For the following sample(s), the artifact detection module 706 may calculate or otherwise determine the recovery value is equal to a reduced percentage (e.g., 60%) of the most recent valid filtered measurement value (or alternatively, a fraction of the preceding recovery value), and so on, thereby dynamically and progressively decreasing the recovery value. Once a filtered measurement value exceeds the recovery value and indicates recovery from the artifact condition, the artifact detection process 800 marks or otherwise indicates that the instant filtered measurement value is valid (task 816). In some embodiments, the artifact detection module 706 may impose a timer or limit on the duration for which the invalid indication is persisted. For example, if more than a threshold number of samples have occurred since the most recent valid filtered measurement value, the artifact detection process 800 may mark or otherwise indicate the instant five-minute filtered measurement value as being valid (e.g., task 816) even though it may not exceed the current recovery value.

Figure 9:
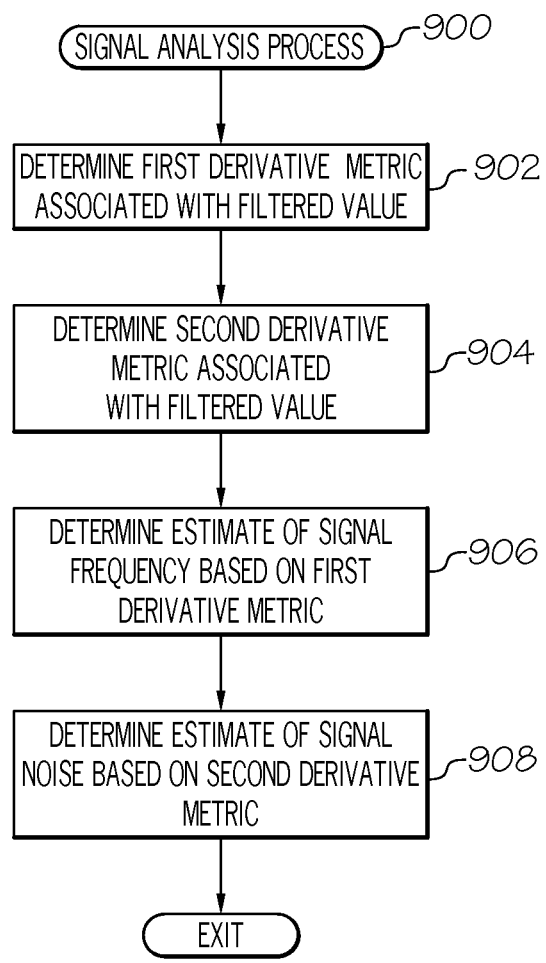
FIG. 9 is a flow diagram of an exemplary signal analysis process suitable for implementation by the signal analysis module in the signal processing system of FIG. 7.

FIG. 9 depicts an exemplary signal analysis process 900 suitable for implementation by the sensing arrangement 504, 600 to calculate or otherwise determine metrics indicative of signal characteristics associated with a measurement signal. The various tasks performed in connection with the signal analysis process 900 may be performed by hardware, firmware, software executed by processing circuitry, or any combination thereof. For illustrative purposes, the following description refers to elements mentioned above in connection with FIGS. 1-7. In practice, portions of the signal analysis process 900 may be performed by different elements of the sensing arrangement 504, 600 and/or control system 500. That said, in exemplary embodiments described herein, the signal analysis process 900 is performed by the signal analysis module 710 of the data management application 610 implemented by the control module 602. It should be appreciated that the signal analysis process 900 may include any number of additional or alternative tasks, the tasks need not be performed in the illustrated order and/or the tasks may be performed concurrently, and/or the signal analysis process 900 may be incorporated into a more comprehensive procedure or process having additional functionality not described in detail herein. Moreover, one or more of the tasks shown and described in the context of FIG. 9 could be omitted from a practical embodiment of the signal analysis process 900 as long as the intended overall functionality remains intact.

In the illustrated embodiment, the signal analysis process 900 calculates or otherwise determines a first derivative metric associated with the instant (or most recent) filtered measurement value (task 902). In this regard, the signal analysis module 710 determines the value of the first derivative associated with the current filtered measurement value in the buffer 708 based on the difference between the current filtered measurement value and the immediately preceding filtered measurement value in the buffer 708 (e.g., by subtracting the preceding filtered measurement value from the current filtered measurement value). In one or more embodiments, the signal analysis module 710 stores or otherwise maintains the first derivative value associated with each respective filtered measurement value in the buffer 708 or elsewhere in memory 608. In exemplary embodiments, the signal analysis module 710 calculates the first derivative metric associated with the current filtered measurement value by averaging the respective first derivative values associated with each of the five-minute filtered measurement values in the buffer 708, then determining the absolute value (or magnitude) of the average first derivative value. Thus, the first derivative metric associated with the current filtered measurement value corresponds to the absolute value of the average for the first derivative of the filtered measurement signal over the preceding interval of time corresponding to the measurement values in the buffer 708 (e.g., the preceding 40 minutes for the case of 8 samples obtained at 5 minute intervals). That said, in alternative embodiments, the first derivative value associated with the current filtered measurement value (e.g., the difference between the current filtered measurement value and the immediately preceding filtered measurement value) may be utilized as the first derivative metric rather than averaging all of the first derivative values associated with five-minute filtered measurement values in the buffer 708. It should be noted that in practice, any measurement values in the buffer 708 that are flagged as being invalid may be excluded from the calculations when determining the first derivative metric. In this regard, in some embodiments, the signal analysis module 710 may perform interpolation or another similar technique to account for invalid measurements in the buffer 708.

In a similar manner, the signal analysis process 900 also calculates or otherwise determines a second derivative metric associated with the instant (or most recent) filtered measurement value (task 904). In this regard, the signal analysis module 710 determines the value of the second derivative associated with the most recent five-minute filtered measurement value in the buffer 708 based on the difference between the first derivative value associated with the most recent filtered measurement value and the first derivative associated with the immediately preceding filtered measurement value in the buffer 708 (e.g., by subtracting the first derivative value associated with the preceding filtered measurement value from the first derivative value associated with the instant filtered measurement value). In one or more embodiments, the signal analysis module 710 also stores or otherwise maintains the second derivative value associated with each respective filtered measurement value in the buffer 708 or elsewhere in memory 608. In exemplary embodiments, the signal analysis module 710 calculates the second derivative metric associated with the current filtered measurement value by determining the average magnitude of the respective second derivative values associated with each of the five-minute filtered measurement values in the buffer 708. Before averaging the second derivative values, the absolute value (or magnitude) of the second derivative values is obtained. Thus, the second derivative metric associated with the current filtered measurement value corresponds to the average magnitude for the second derivative of the filtered measurement signal over the preceding interval of time corresponding to the measurement values in the buffer 708. That said, in some embodiments, the second derivative value associated with the current filtered measurement value (e.g., the difference between the first derivative values for the most recent five-minute filtered measurement value and the immediately preceding five-minute filtered measurement value) may be utilized as the second derivative metric without averaging all of the second derivative values. For example, in some embodiments, the greater of the second derivative value associated with the instant filtered measurement value and the average magnitude of the second derivative values associated with all of the filtered measurement values in the buffer 708 is used as the second derivative metric. As described above, in practice, measurement values in the buffer 708 that are flagged as being invalid may be excluded from the calculations when determining the second derivative metric, and first derivative values determined using interpolation or another similar technique may be utilized to account for invalid measurements in the buffer 708.

The signal analysis process 900 continues by calculating or otherwise determining an estimate of the frequency of the filtered measurement signal based at least in part on the first derivative metric (task 906). For example, in accordance with one embodiment, the signal analysis module 710 determines an estimated signal frequency metric by multiplying or otherwise scaling the first derivative metric by the calibration factor currently being utilized to convert the output from the adaptive filtering module 714 into a blood glucose value, and then clips the result such that the estimated signal frequency metric does not exceed an upper limit (e.g., 4). In some embodiments, the signal analysis module 710 may also impose a floor so that the estimated signal frequency does not fall below a lower limit (e.g., 0.2).

The signal analysis process 900 also calculates or otherwise determines an estimate of the noise present in the filtered measurement signal based at least in part on the second derivative metric (task 908). In a similar manner as described above, the signal analysis module 710 determines an estimated signal noise metric by multiplying or otherwise scaling the second derivative metric by the current calibration factor, and then clips the result such that the estimated signal noise metric does not exceed 10. In one or more embodiments, the signal analysis module 710 determines the estimated signal noise metric using the larger of the second derivative value associated with the current filtered measurement value and the second derivative metric associated with the current filtered measurement value. In this regard, when the second derivative value associated with the current filtered measurement value is greater than the average magnitude for the second derivative of the filtered measurement signal over the preceding interval of time corresponding to the measurement values in the buffer 708, the signal analysis module 710 determines the estimated signal noise metric by multiplying or otherwise scaling the second derivative value by the current calibration factor and clipping the result instead of using the averaged second derivative value.

Figure 10:
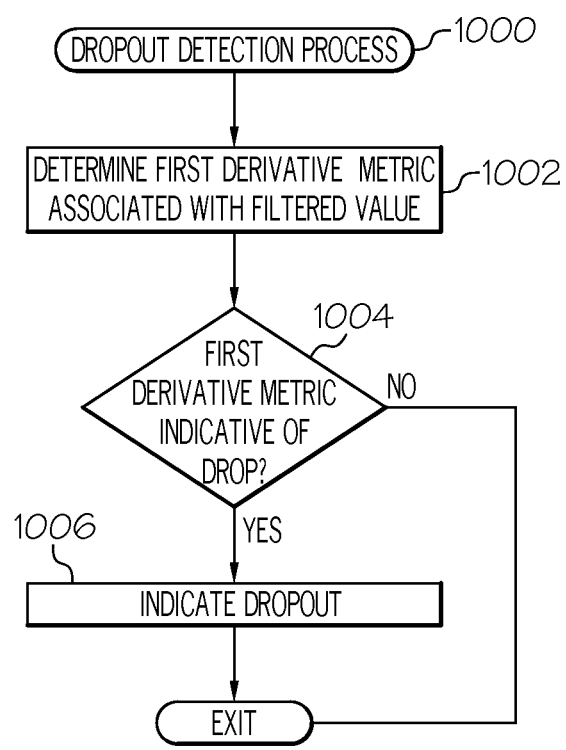
FIG. 10 is a flow diagram of an exemplary dropout detection process suitable for implementation by the dropout detection module in the signal processing system of FIG. 7.

FIG. 10 depicts an exemplary dropout detection process 1000 suitable for implementation by the sensing arrangement 504, 600 to detect or otherwise identify presence of a dropout condition in the measurement signal. The various tasks performed in connection with the dropout detection process 1000 may be performed by hardware, firmware, software executed by processing circuitry, or any combination thereof. For illustrative purposes, the following description refers to elements mentioned above in connection with FIGS. 1-7. In practice, portions of the dropout detection process 1000 may be performed by different elements of the sensing arrangement 504, 600 and/or control system 500. That said, in exemplary embodiments described herein, the dropout detection process 1000 is performed by the dropout detection module 712 of the data management application 610 implemented by the control module 602. It should be appreciated that the dropout detection process 1000 may include any number of additional or alternative tasks, the tasks need not be performed in the illustrated order and/or the tasks may be performed concurrently, and/or the dropout detection process 1000 may be incorporated into a more comprehensive procedure or process having additional functionality not described in detail herein. Moreover, one or more of the tasks shown and described in the context of FIG. 10 could be omitted from a practical embodiment of the dropout detection process 1000 as long as the intended overall functionality remains intact.

In exemplary embodiments, the dropout detection process 1000 determines a first derivative metric associated with the instant (or most recent) filtered measurement value and detects or otherwise identifies a dropout condition when the first derivative metric is indicative of a relatively large drop or a relatively quick drop in the filtered measurement value (tasks 1002, 1004). When the first derivative metric associated with the instant filtered measurement value is indicative of a relatively large or relatively quick drop in the filtered measurement signal, the dropout detection process 1000 detects a dropout condition and generates or otherwise provides indication of the dropout condition (task 1006). In this regard, the dropout detection module 712 provides a signal or notification to the adaptive filtering module 714 identifying the likely presence of a dropout condition, and in response, the adaptive filtering module 714 dynamically adjusts the filtering of the filtered measurement signal in a manner that mitigates or otherwise remediates the dropout condition, as described in greater detail below.

In one embodiment, the dropout detection module 712 identifies a dropout condition when the first derivative metric is greater than a first threshold value and a second derivative metric is less than a second threshold value having magnitude of the second threshold value is less than the first threshold value, such that the dropout detection module 712 identifies a dropout condition when the filtered measurement signal abruptly drops to an abnormally low reading that is more likely to be attributable to transient behavior in the user's body or the sensing element 604 than an artifact condition. In one or more embodiments, the dropout detection module 712 obtains the first and second derivative metrics determined by the signal analysis module 710 and stored in association with the instant five-minute filtered measurement in the buffer 708 and/or memory 608. In alternative embodiments, the dropout detection module 712 calculates the first and second derivative metrics independently.

In exemplary embodiments, the dropout detection module 712 calculates or otherwise determines the first derivative metric by multiplying a difference between the instant filtered measurement value and the preceding filtered measurement value (e.g., the first derivative associated with the instant filtered measurement value) by the current calibration factor. The dropout detection module 712 may also calculate or otherwise determine the second derivative metric by multiplying the second derivative associated with the instant filtered measurement value (e.g., a difference between the derivative associated with the instant filtered measurement value and the derivative associated with the immediately preceding filtered measurement value) by the current calibration factor. In one embodiment, the dropout detection module 712 detects a dropout condition in response to a relatively large drop in the filtered measurement signal when the first derivative metric associated with the instant filtered measurement value is less than −5 mg/dL/min while the absolute value (or magnitude) of the second metric associated with the instant filtered measurement value is less than 1 mg/dL/min/min and the absolute value (or magnitude) first derivative metric associated with the immediately preceding filtered measurement value is less than 0.75 mg/dL/min. The dropout detection module 712 may also detects a dropout condition in response to a relatively moderate drop in the filtered measurement signal when the first derivative metric associated with the instant filtered measurement value is less than −0.75 mg/dL/min while the noise metric (e.g., from task 908) associated with the filtered measurement signal is less than 1 and the first derivative metric associated with the immediately preceding filtered measurement value is greater than −0.5 mg/dL/min. Additionally, the dropout detection module 712 may also detect a dropout condition in response to a relatively quick change in the direction of the filtered measurement signal when the first derivative metric associated with the instant filtered measurement value is less than −2.5 mg/dL/min while the noise metric (e.g., from task 908) associated with the filtered measurement signal is less than 1 and the first derivative metric associated with the immediately preceding filtered measurement value is greater than 0 mg/dL/min.

Figure 11:
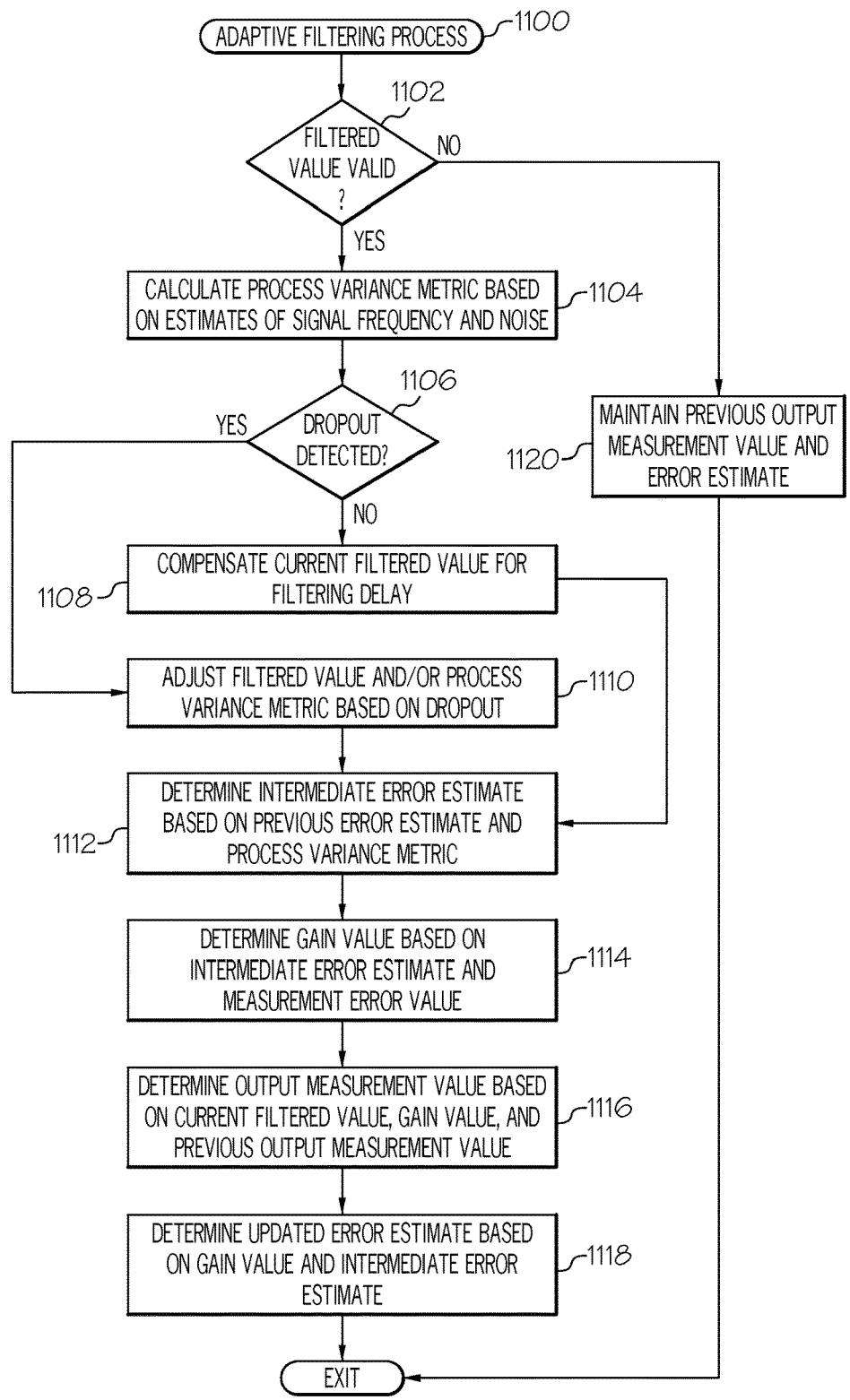
FIG. 11 is a flow diagram of an exemplary adaptive filtering process suitable for implementation by the adaptive filtering module in the signal processing system of FIG. 7.

FIG. 11 depicts an exemplary adaptive filtering process 1100 suitable for implementation by the sensing arrangement 504, 600 to detect or otherwise identify presence of a dropout condition in the measurement signal. The various tasks performed in connection with the adaptive filtering process 1100 may be performed by hardware, firmware, software executed by processing circuitry, or any combination thereof. For illustrative purposes, the following description refers to elements mentioned above in connection with FIGS. 1-7. In practice, portions of the adaptive filtering process 1100 may be performed by different elements of the sensing arrangement 504, 600 and/or control system 500. That said, in exemplary embodiments described herein, the adaptive filtering process 1100 is performed by the adaptive filtering module 714 of the data management application 610 implemented by the control module 602. It should be appreciated that the adaptive filtering process 1100 may include any number of additional or alternative tasks, the tasks need not be performed in the illustrated order and/or the tasks may be performed concurrently, and/or the adaptive filtering process 1100 may be incorporated into a more comprehensive procedure or process having additional functionality not described in detail herein. Moreover, one or more of the tasks shown and described in the context of FIG. 11 could be omitted from a practical embodiment of the adaptive filtering process 1100 as long as the intended overall functionality remains intact.

Referring to FIG. 11, and with continued reference to FIGS. 5-10, in exemplary embodiments, the adaptive filtering process 1100 is performed each time the buffer 708 is updated with a new filtered measurement value (e.g., once every 5 minutes). The illustrated process 1100 begins by verifying or otherwise confirming the current (or most recent) filtered measurement value is valid and usable (task 1102). In this regard, the adaptive filtering module 714 verifies the newest filtered measurement value in the buffer 708 is not flagged or otherwise marked as invalid before proceeding with processing the value. When the current filtered measurement value is invalid, the adaptive filtering process 1100 maintains the same output measurement value and error estimate that were output and fed back from the preceding iteration of the adaptive filtering process 1100 (task 1120), as described in greater detail below. In this regard, the adaptive filtering module 714 outputs the measurement value and error estimate that were fed back from the previous iteration without performing any processing on the invalid measurement value. Additionally, in one or more embodiments, when the current filtered measurement value is the initial measurement value input to the adaptive filtering module 714 (e.g., the first value after powering on and/or resetting the sensing device 600), the adaptive filtering process 1100 outputs the current filtered measurement value and exits without any further processing on the current filtered measurement value. It should be noted that in some embodiments, where the infusion device 502 and/or pump control system 520 are configured to present a graphical representation of the user's sensed glucose value on a display (e.g., user interface element 540), maintaining the previously output measurement for use in determining the sensed glucose value improves the user experience by eliminating or otherwise reducing the visibility of rapid and/or large transient changes in the displayed sensed glucose value that could otherwise alarm the user or cause the user to take unnecessary action(s).

When the current filtered measurement value is valid and not the initial measurement value input to the adaptive filtering module 714, the adaptive filtering process 1100 continues by calculating or otherwise determining a value for a process variance metric based on the estimates of the signal characteristics for the filtered measurement signal (task 1104). In this regard, the adaptive filtering module 714 calculates the process variance metric based on the estimates of the signal frequency and signal noise associated with the filtered measurement signal obtained from the signal analysis module 710. In one embodiment, the adaptive filtering module 714 calculates a first variable ($c_1$) based on the signal frequency estimate ($f_e$) using equation $c_1 = a_1 \times f_e - b_1$, and calculates a second variable ($c_2$) based on the signal frequency estimate ($f_e$) using equation $c_2 = a_2 \ln(f_e) - b_2$. The adaptive filtering module 714 continues by calculating the process variance metric (Q) based on the signal frequency estimate ($f_e$) and the signal noise estimate ($n_e$) using equation $Q=c_1 \times e^{(c^2 \times n_e)}$. In exemplary embodiments, $a_1$, $a_2$, $b_1$ and $b_2$ are scalar values chosen to reduce the difference (or error) between the output of the adaptive filtering module 714 and a known reference input signal (e.g., a sine wave signal).

The illustrated process 1100 continues by identifying or otherwise determining whether a dropout condition has been detected, and in the absence of a dropout condition, adjusting the input filtered measurement value to compensate for the lag or delay associated with the filtering being performed by the signal processing system (tasks 1106, 1108). In this regard, the adaptive filtering module 714 calculates or otherwise determines a modified rate of change for the filtered measurement signal based at least in part on the first derivative metric associated with the current filtered measurement value and modifies the current filtered measurement value using the modified rate of change when the signal noise estimate ($n_e$) is less than an upper noise threshold value. For example, in one embodiment, the adaptive filtering module 714 modifies the current filtered measurement value using the signal noise estimate ($n_e$) when the signal noise estimate ($n_e$) is less than or equal to the upper noise threshold value of 3 and greater than 1 (e.g., when $1 < n_e \leq 3$) using equation $i_{adj} = i_{sig} + 5(roc \times (1.5 - 0.5 n_e))$, where roc is the modified rate of change having a value between $-1$ and 1, $i_{sig}$ is the current filtered measurement value, and $i_{adj}$ is the adjusted filtered measurement value. Alternatively, when the signal noise estimate ($n_e$) is less than 1, the adaptive filtering module 714 determines the adjusted filtered measurement value using equation $i_{adj} = i_{sig} + 5 \times roc$. In exemplary embodiments, when the signal noise estimate ($n_e$) is greater than the upper noise threshold value, the adaptive filtering module 714 does not adjust or otherwise modify the current filtered measurement value based on the modified rate of change (e.g., $i_{adj} = i_{sig}$).

In exemplary embodiments, the modified rate of change is determined as a weighted sum of the first derivative associated with the instant filtered measurement value (e.g., the difference between the instant filtered measurement value and the immediately preceding filtered measurement value in buffer 708) and the first derivative metric associated with the filtered measurement values in the buffer 708 (e.g., the first derivative metric from the signal analysis module 710 that was determined at 902). In exemplary embodiments, when the magnitude of the modified rate of change is greater than a maximum value, the modified rate of change is set to be equal to zero, such that $i_{adj} = i_{sig}$. When the magnitude of the modified rate of change is less than the maximum value, the adaptive filtering module 714 clips the modified rate of change so that its magnitude is less than or equal to a fraction (or percentage) of the maximum value. For example, in one embodiment, the adaptive filtering module 714 clips the modified rate of change to values between $-1$ mg/dL/min and 1 mg/dL/min.

In response to detecting a dropout condition, in exemplary embodiments, the adaptive filtering process 1100 continues by adjusting or otherwise modifying the filtered measurement value and/or the process variance metric (task 1110). In this regard, when the dropout condition is detected, the adaptive filtering module 714 adds an offset to the filtered measurement value to mitigate or otherwise compensate for the dropout condition. Additionally, the adaptive filtering module 714 determines an alternative process variance metric value in response to the dropout condition and substitutes the alternative process variance metric value for the calculated process variance metric (Q) when the alternative process variance metric value is less than the calculated process variance metric. In exemplary embodiments, the adaptive filtering module 714 implements a counter that tracks the number of filtered measurement values since the dropout condition to progressively decrease the offset and progressively increase the alternative process variance metric value to phase out the dropout modifications. For example, when the dropout condition is initially identified by the dropout detection module 712, the adaptive filtering module 714 may increment the counter from zero to one. Thereafter, the adaptive filtering module 714 calculates or otherwise determines the dropout offset and the alternative process variance metric value based on the value of the counter, adds the dropout offset to the filtered measurement value to obtain a dropout compensated filtered measurement value, and substitutes the alternative process variance metric value for the calculated process variance metric value when the alternative process variance metric value is less than the calculated process variance metric value.

In exemplary embodiments, the equations for calculating the dropout offset and the alternative process variance metric value are configured such that the dropout offset decreases and the alternative process variance metric value increases as the value of the counter increases. In this manner, if the dropout condition is still identified on subsequent samples, the added dropout offset will be progressively reduced for each sample towards zero while the alternative process variance metric value progressively increases for each sample by incrementing the value of the counter. Once a dropout condition is no longer identified, the adaptive filtering module 714 may clear or otherwise reset the dropout counter to zero. Additionally, in some embodiments, the adaptive filtering module 714 may automatically stop adjusting the filtered measurement value and/or the process variance metric when the value of dropout counter is greater than an upper threshold number of measurement samples. It should be noted that in some embodiments, where the infusion device 502 and/or pump control system 520 are configured to present a graphical representation of the user's sensed glucose value on a display (e.g., user interface element 540), using a dropout compensated filtered measurement for determining the output measurement (which is subsequently converted to the sensed glucose value using a calibration factor) improves the user experience by eliminating or otherwise reducing the visibility of dropouts in the displayed sensed glucose value that could otherwise alarm the user or cause the user to take unnecessary action(s).

Still referring to FIG. 11, in exemplary embodiments, the adaptive filtering process 1100 continues by calculating or otherwise determining an intermediate error estimate based on the output error estimate from the preceding iteration of the adaptive filtering process 1100 and the process variance metric (task 1112). In exemplary embodiments, the adaptive filtering module 714 determines the intermediate error estimate ($p_i$) by adding the process variance metric to the output error estimate ($p_{out}[n-1]$) from the preceding iteration of the adaptive filtering process 1100 that was fed back to the adaptive filtering module 714 (e.g., $p = p_{out}[n-1] + Q$). The adaptive filtering process 1100 continues by calculating or otherwise determining a gain value based on the intermediate error estimate and a measurement error value (task 1114). In this regard, the measurement error value represents noise attributable to electromagnetic interference, movement of the sensing element 604, or interference caused by other non-glucose molecules in the interstitial fluid. In exemplary embodiments, the adaptive filtering module 714 determines a Kalman gain value (k) using the equation $k = p_i / (p_i + r)$, where r represents the measurement error value. In one embodiment, the measurement error value is a fixed value equal to one.

After determining the filter gain value, the adaptive filtering process 1100 continues by calculating or otherwise determining the output measurement value based on the current filtered measurement value, the filter gain value, and the previous output measurement value (task 1116). In exemplary embodiments, the adaptive filtering module 714 determines the output measurement value according to the equation $i_{out} = i_{out}[n-1] + k(i_{sig} - i_{out}[n-1])$, where $i_{out}$ is the output measurement value, $i_{out}[n-1]$ represents the preceding output measurement value, and $i_{sig}$ represents the current (or most recent) filtered measurement value input to the adaptive filtering module 714 as modified pursuant to any adjustments for filtering delay (task 1106) and/or dropout conditions (task 1110) that were made to the input filtered measurement value as described above. The adaptive filtering process 1100 also calculates or otherwise determines an updated output error estimate based on the filter gain value and the intermediate error estimate (task 1118). In exemplary embodiments, the adaptive filtering module 714 determines the output error estimate ($p_{out}$) according to the equation using the equation $p_{out} = p_i(1-k)$.

Referring again to FIGS. 5-7, the output filtered measurement value and the output error estimate determined by the adaptive filtering module 714 are fed back or otherwise maintained by the adaptive filtering module 714 for use in determining the subsequent output filtered measurement value based on the preceding output filtered measurement value and the preceding output error estimate. In exemplary embodiments described herein, the output filtered measurement value is provided to the calibration application 612 for calculating or otherwise determining a calibration factor for converting the uncalibrated output filtered measurement value to a sensor glucose value. Additionally, the output filtered measurement value is also provided to the health monitoring application 614 for determining when a maintenance condition exists with respect to the sensing element 604. In some embodiments, the uncalibrated output filtered measurement value is also provided to the pump control system 520 and/or a user interface 540 (e.g., via the output interface 606) for determining dosage commands for operating the motor 507 of the infusion device 502, displaying or otherwise presenting a graphical representation or other indication of the sensed glucose level in the body 501 of the user, and/or the like.

Figure 12:
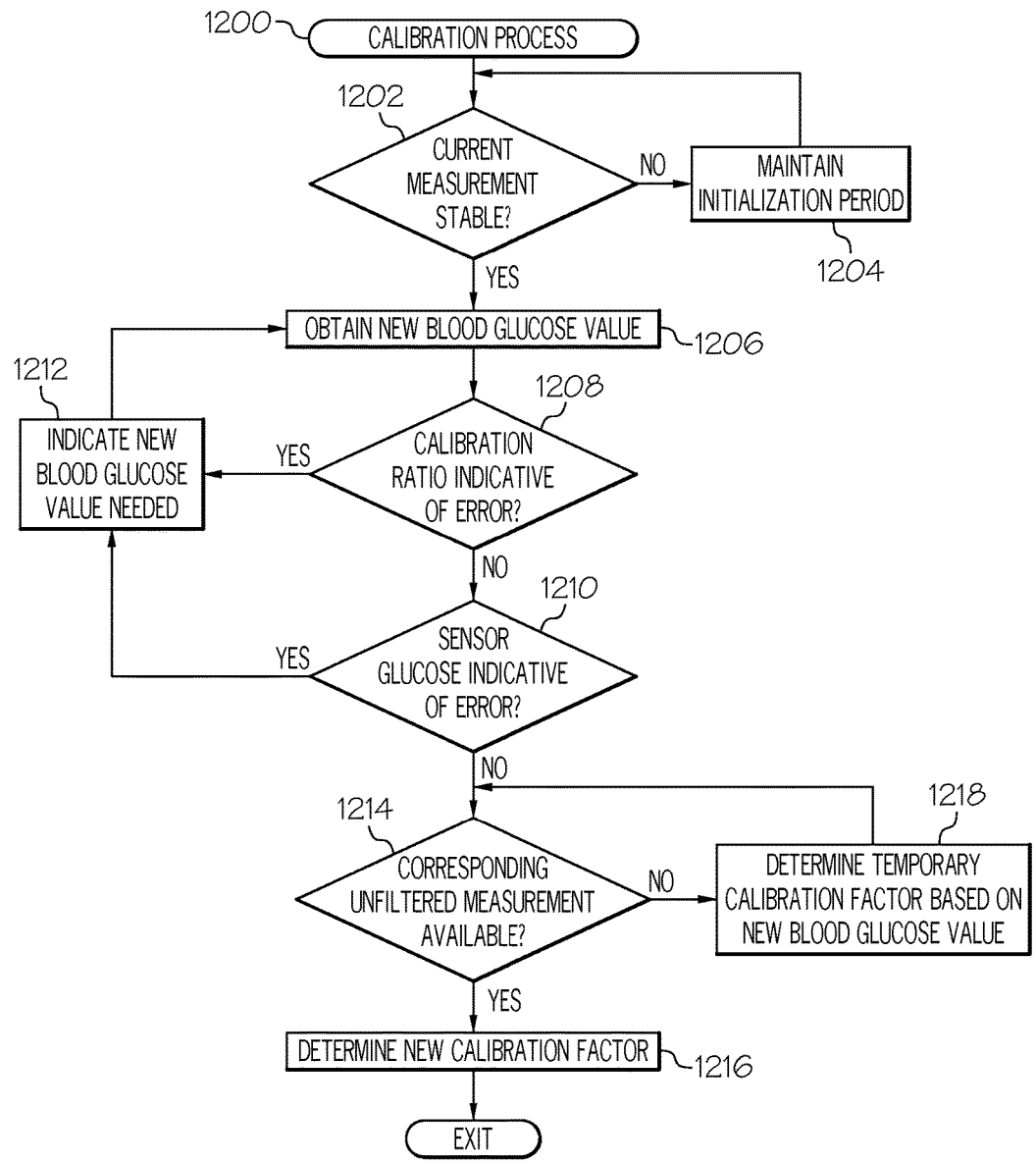
FIG. 12 is a flow diagram of an exemplary calibration process suitable for implementation by the calibration application in the sensing arrangement of FIG. 6.

FIG. 12 depicts an exemplary calibration process 1200 for calibrating a sensing arrangement 504, 600 for converting the uncalibrated measurement values determined based on electrical signals output by the sensing element 604 into corresponding calibrated measurement values. The various tasks performed in connection with the calibration process 1200 may be performed by hardware, firmware, software executed by processing circuitry, or any combination thereof. For illustrative purposes, the following description refers to elements mentioned above in connection with FIGS. 1-7. In practice, portions of the calibration process 1200 may be performed by different elements of the sensing arrangement 504, 600 and/or the control system 500. That said, in exemplary embodiments described herein, the calibration process 1200 is performed by the calibration application 612 implemented by the control module 602. It should be appreciated that the calibration process 1200 may include any number of additional or alternative tasks, the tasks need not be performed in the illustrated order and/or the tasks may be performed concurrently, and/or the calibration process 1200 may be incorporated into a more comprehensive procedure or process having additional functionality not described in detail herein. Moreover, one or more of the tasks shown and described in the context of FIG. 12 could be omitted from a practical embodiment of the calibration process 1200 as long as the intended overall functionality remains intact.

In exemplary embodiments, the calibration process 1200 begins by analyzing the uncalibrated measurements during an initialization period to detect or otherwise identify when the uncalibrated measurements are stable and maintains the initialization period while the uncalibrated measurements are unstable (tasks 1202, 1204). In this regard, the initialization period imposed by the calibration process 1200 delays calibration of the sensing arrangement 504, 600 until the electrical signals generated by the sensing element 604 stabilize. In exemplary embodiments, the calibration application 612 determines the uncalibrated measurements are stable when a number of consecutive measurements output by the data management application 610 are within a predetermined range of values and a difference or change between successive measurements is less than a threshold amount. For example, in one embodiment, the calibration application 612 determines the uncalibrated measurements are stable when three consecutive measurements output by the data management application 610 are within a range of measurement values and the differences between successive measurements of the three consecutive measurements are less than a threshold percentage of the preceding measurement of the pair. In this regard, the calibration application 612 detects that the uncalibrated measurements are stable when the most recent uncalibrated measurement from the data management application 610 is within the threshold percentage of the preceding measurement, which is within the threshold percentage of the next preceding measurement, and each of those three most recent uncalibrated measurements from the data management application 610 is within a particular range of values. Once the uncalibrated measurements are stable, the calibration application 612 may indicate to the pump control system 520 that the user may be notified that the sensing arrangement 504, 600 is ready for calibration. Alternatively, the calibration application 612 may generate a user notification that the sensing arrangement 504, 600 is ready for calibration via an output user interface 606.

After confirming the uncalibrated measurements are stable, the calibration process 1200 proceeds by receiving or otherwise obtaining a new reference measurement value and detecting or otherwise identifying whether an error condition exists based at least in part on the new reference measurement value (tasks 1206, 1208, 1210). In this regard, the user may manipulate the blood glucose meter 530 to obtain a new blood glucose measurement from the user's body 501 and transmit or otherwise provide the new blood glucose measurement value to the calibration application 612 and/or sensing arrangement 504, 600. In response to identifying an error condition, the calibration process 1200 generates or otherwise provide a user notification that indicates a new reference measurement value needs to be obtained for calibration (task 1212). In this regard, the calibration application 612 generates or otherwise provides an indication to the user via an output user interface element 540 associated with the infusion device 502 (e.g., via pump control system 520) and/or an output interface 606 associated with the sensing arrangement 504, 600.

In exemplary embodiments, the calibration application 612 calculates or otherwise determines one or more calibration ratios associated with the new blood glucose measurement value and detects or otherwise identifies whether the calibration ratio(s) are indicative of an error condition (e.g., task 1208). In this regard, the calibration application 612 identifies an error condition when a calibration ratio associated with the new blood glucose measurement value is not within a range of acceptable values. For example, the calibration application 612 may determine a first calibration ratio, alternatively referred to herein as a current calibration ratio, by dividing the new blood glucose measurement value by the sum of the most recent filtered measurement value from the data management application 610 and/or adaptive filtering module 714 and an offset value. The offset value represents the baseline current for the sensing element 604 (e.g., the nominal current output by the sensing element 604 in the absence of any measurable glucose). The calibration application 612 may also determine one or more predicted calibration ratios by dividing the new blood glucose measurement value by the sum of a predicted measurement value and the offset value. In this regard, the predicted measurement value represents the expected measurement value from the data management application 610 and/or adaptive filtering module 714 at some point in the future that will be paired with the new blood glucose measurement value for determining the calibration factor. In exemplary embodiments, if any of the current calibration ratio or the predicted calibration ratios is outside of the allowable range of calibration factor values, the calibration application 612 generates or otherwise provides a notification indicative of a need to re-obtain a new blood glucose measurement with the blood glucose meter 530 as described above.

In exemplary embodiments, the calibration application 612 also compares the current calibration ratio to the calibration factor currently being utilized by the pump control system 520 and/or sensing arrangement 504, 600 and detects or otherwise identifies an error condition when the difference between the current calibration ratio and the current calibration factor is greater than a threshold amount (e.g., a percentage of the current calibration factor). Similarly, the calibration application 612 also compares the current calibration ratio to the preceding calibration ratio (e.g., the preceding reference blood glucose measurement value from the blood glucose meter 530 divided by its paired uncalibrated filtered measurement value) and detects or otherwise identifies an error condition when the difference between the current calibration ratio and the preceding calibration ratio is greater than a threshold amount (e.g., a percentage of the preceding calibration ratio).

In exemplary embodiments, the calibration application 612 also calculates or otherwise determines a difference between the new blood glucose measurement value and the most recent sensed measurement value determined based on the most recent filtered measurement value and the current calibration factor and detects or otherwise identifies an error condition when the difference exceeds a threshold value (e.g., task 1210). For example, in one embodiment, the calibration application 612 detects an error condition when the difference between the new blood glucose measurement value and the most recent sensed measurement value is greater than a threshold glucose concentration value.

After confirming an error condition does not exist, the calibration process 1200 continues by identifying or otherwise determining whether a corresponding unfiltered measurement value for pairing with the new blood glucose measurement value is available (task 1214). In this regard, in one or more exemplary embodiments, the calibration application 612 implements a timer or another similar feature and waits for at least a threshold duration of time before selecting the next filtered measurement value from the data management application 610 and/or the adaptive filtering module 714 for pairing with a reference blood glucose measurement value. For example, in one embodiment, the calibration application 612 waits for at least ten minutes from the time of the reference blood glucose measurement value before selecting the next filtered measurement value from the data management application 610 and/or the adaptive filtering module 714 for pairing with the reference blood glucose measurement value. After the threshold amount of time has elapsed, the calibration process 1200 pairs the next valid unfiltered measurement value with the reference blood glucose measurement value and calculates or otherwise determines a new (or updated) calibration factor for converting the uncalibrated measurement values into calibrated values based on the new reference blood glucose measurement value and its paired uncalibrated measurement value (task 1216), as described in greater detail below in the context of the calibration factor determination process 1300 of FIG. 13.

In exemplary embodiments, when an unfiltered measurement value is not yet available for pairing, the calibration process 1200 dynamically adjusts the calibration factor towards an expected calibration factor indicated by the relationship between the new reference blood glucose measurement value and the uncalibrated measurement value(s) received after the new reference blood glucose measurement value was obtained (task 1218). In this regard, during the period where the calibration application 612 is waiting for an unfiltered measurement value for pairing, the calibration application 612 may determine an adjusted calibration factor that is used by the sensing arrangement 504, 600 and/or the pump control system 520 to convert any filtered measurement values output by the data management application 610 and/or the adaptive filtering module 714 during that period into a sensed measurement value (e.g., for presenting the sensed glucose value on a display 540 and/or determining delivery commands during the ten minute waiting period). In one embodiment, the calibration application 612 temporarily pairs the new reference blood glucose measurement value with an updated filtered measurement value output by the data management application 610 and/or the adaptive filtering module 714 and calculates an intermediate calibration factor based on the temporary pairing and stored pairings of reference blood glucose measurement values and filtered measurement values in a similar manner as described in greater detail below (e.g., task 1310). In this regard, the intermediate calibration factor represents an expected calibration factor if the new reference blood glucose measurement value were to be paired with an uncalibrated measurement value equal to the current output from the data management application 610 and/or the signal analysis module 710.

In exemplary embodiment, the calibration application 612 determines an adjusted calibration factor as a weighted sum of the intermediate calibration factor and the calibration factor currently being utilized by the sensing arrangement 504, 600 and/or the pump control system 520. For example, in one embodiment, the calibration application 612 weights the intermediate calibration factor with the current calibration factor by multiplying the intermediate calibration factor by 70%, multiplying the current calibration factor by 30%, and adding the two products to obtain the adjusted calibration factor. In exemplary embodiments, the calibration application 612 dynamically adjusts the calibration factor towards the expected calibration factor by substituting the adjusted calibration factor for use in lieu of the current calibration factor based on one or more derivative metrics associated with filtered measurement values from the data management application 610 and/or the adaptive filtering module 714. In this regard, if the product of the first derivative metric associated with the current (or most recent) filtered measurement value in the buffer 708 and the current calibration factor is greater than one, the calibration application 612 selects the lesser of the current calibration factor and the adjusted calibration factor for use in determining a sensed glucose value based on the current uncalibrated measurement value from the data management application 610 and/or the adaptive filtering module 714. Conversely, if the product of the first derivative metric associated with the current (or most recent) filtered measurement value in the buffer 708 and the current calibration factor is less than one, the calibration application 612 selects the greater of the current calibration factor and the adjusted calibration factor for use in determining a sensed glucose value based on the current uncalibrated measurement value from the data management application 610 and/or the adaptive filtering module 714.

Figure 13:
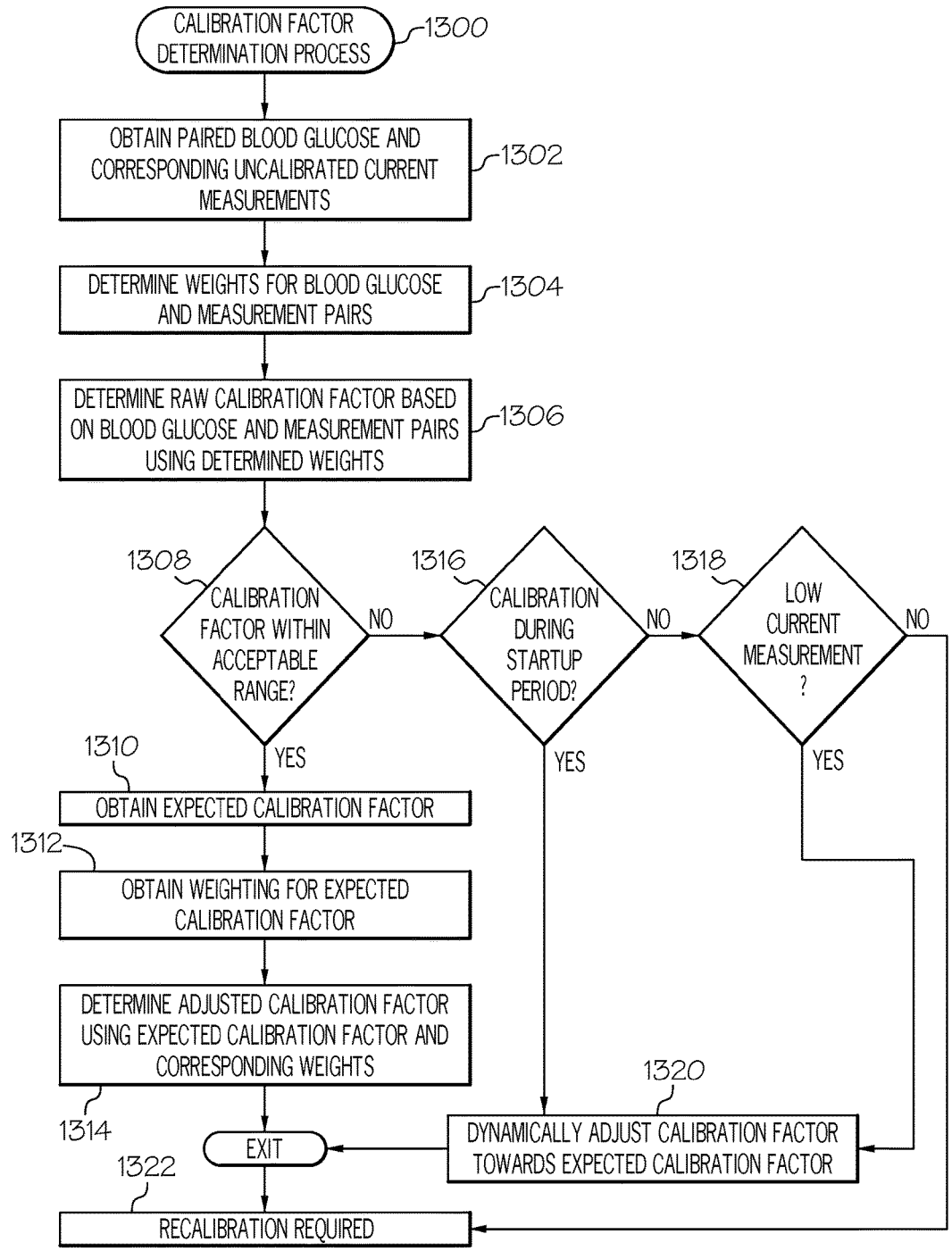
FIG. 13 is a flow diagram of an exemplary calibration factor determination process suitable for implementation in conjunction with the calibration process of FIG. 12.

FIG. 13 depicts an exemplary calibration factor determination process 1300 for determining a calibration factor used to convert uncalibrated measurement values subsequently output by a sensing arrangement 504, 600 into corresponding calibrated measurement values. In one or more exemplary embodiments, the calibration factor determination process 1300 is performed at task 1216 of the calibration process 1200 of FIG. 12. The various tasks performed in connection with the calibration factor determination process 1300 may be performed by hardware, firmware, software executed by processing circuitry, or any combination thereof. For illustrative purposes, the following description refers to elements mentioned above in connection with FIGS. 1-7. In practice, portions of the calibration factor determination process 1300 may be performed by different elements of the sensing arrangement 504, 600 and/or the control system 500. That said, in exemplary embodiments described herein, the calibration factor determination process 1300 is performed by the calibration application 612 implemented by the control module 602. It should be appreciated that the calibration factor determination process 1300 may include any number of additional or alternative tasks, the tasks need not be performed in the illustrated order and/or the tasks may be performed concurrently, and/or the calibration factor determination process 1300 may be incorporated into a more comprehensive procedure or process having additional functionality not described in detail herein. Moreover, one or more of the tasks shown and described in the context of FIG. 13 could be omitted from a practical embodiment of the calibration factor determination process 1300 as long as the intended overall functionality remains intact.

In exemplary embodiments, the calibration factor determination process 1300 begins by obtaining paired reference blood glucose measurement values and corresponding uncalibrated filtered current measurement values, calculating or otherwise determining one or more weighting factors for the respective pairs of blood glucose and uncalibrated measurement values, and calculating or otherwise determining a raw (or unadjusted) calibration factor based on the relationships between the paired measurement values and the respective weighting factors associated therewith (tasks 1302, 1304, 1306). In this regard, in exemplary embodiments, the calibration application 612 implements or otherwise provides a calibration buffer (e.g., in memory 608) that stores or otherwise maintains a number of reference blood glucose measurement values previously received from the blood glucose meter 530 along with the respective paired uncalibrated filtered current measurement value ($i_{out}$) from the data management application 610 and/or the adaptive filtering module 714 that corresponds to that respective blood glucose measurement value (e.g., the $i_{out}$ value that was output between 10 to 15 minutes after the respective blood glucose measurement value was obtained). In one exemplary embodiment, the calibration application 612 updates the calibration buffer to maintain the new reference blood glucose measurement value and its paired uncalibrated filtered current measurement value along with the three preceding pairs of reference blood glucose measurement values and corresponding uncalibrated filtered current measurement values.

In exemplary embodiments, the calibration application 612 determines the raw calibration factor as a ratio of a first weighted sum of the respective products of each respective measurement pair with respect to a second weighted sum of the respective square of each respective uncalibrated measurement value. In this regard, in one or more embodiments, the first weighted sum is a sum of the respective products of each respective reference measurement value, its paired uncalibrated filtered current measurement value, and weighting factors associated with that respective blood glucose-current measurement pair, while the second weighted sum is a sum of the respective products of the square of each respective uncalibrated filtered current measurement value and the weighting factors associated with that measurement's respective blood glucose-current measurement pair. For example, the raw calibration factor ($CF_R$) may be governed by the equation:

$$CF_R = \frac{\sum \alpha_i \beta_i i_{out_i} BG_i}{\sum \alpha_i \beta_i i_{out_i}^2},$$

where $i_{out}$ represents the uncalibrated filtered current measurement value of a respective blood glucose-current measurement pair, $BG_i$ represents the reference blood glucose measurement value of that respective blood glucose-current measurement pair, $\alpha_i$ represents a first weighting factor associated with that respective blood glucose-current measurement pair, and represents a second weighting factor associated with that respective blood glucose-current measurement pair. The $\alpha$ weighting factors generally represent FIR filter coefficients for the calibration ratios associated with the respective blood glucose-current measurement pairs, while the $\beta$ weighting factors compensate for the nonlinearities in the response of the sensing element 604 (e.g., nonlinearities in the relationship between the output signals generated by the sensing element 604 and the actual fluid glucose level).

In one or more embodiments, the calibration application 612 determines the first weighting factor ($\alpha_i$) as a fixed value based on the relative age of the respective blood glucose-current measurement pair. In alternative embodiments, the calibration application 612 may determine the first weighting factors using the equation $\alpha_i = e^{-\Delta t/T}$, where $\Delta t$ represents the amount of time between a respective reference blood glucose measurement value and the preceding reference blood glucose measurement value. In such embodiments, the calibration buffer may also store or otherwise maintain, in association with each respective blood glucose-current measurement pair, the time associated with the respective blood glucose-current measurement pair. In this regard, fixed values may be utilized to emulate exponential decay in lieu of deterministically calculating the first weighting factor using an exponential decay function. In one or more embodiments, the calibration application 612 determines the second weighting factor ($\beta_i$) as a function of the reference blood glucose measurement value of the respective blood glucose-current measurement pair. For example, the calibration application 612 may calculate the second weighting factor using the equation $\beta_i = g_i BG_i^{-g_2} - g_3$, where $g_1$ represents a linear scaling factor for the glucose response of the sensing element 604, $g_2$ represents an exponential scaling factor for the glucose response of the sensing element 604, and $g_3$ represents an offset value for the glucose response of the sensing element 604. After determining the weighting factors for each of the respective blood glucose-current measurement pairs in the calibration buffer, the calibration application 612 then calculates the raw calibration factor ($CF_R$) as the ratio of the weighted sums described above.

Still referring to FIG. 13, in exemplary embodiments, the calibration factor determination process 1300 continues by identifying or otherwise determining whether the raw calibration factor is within an acceptable range of values (task 1308). When the value of the raw calibration factor is acceptable, the calibration factor determination process 1300 continues by obtaining or otherwise identifying an expected calibration factor for the sensing arrangement and a weighting factor for the expected calibration factor, and determining an adjusted calibration factor based on the raw calibration factor, the expected calibration factor, and the weighting for the expected calibration factor (1310, 1312, 1314). In this manner, the calibration factor determination process 1300 effectively normalizes the raw calibration factor to account for potential inaccuracies in the reference blood glucose measurement value(s) and/or the uncalibrated filtered current measurement value(s) that could be caused by normal variations in sensitivities or other transient events. The expected calibration factor represents the anticipated or likely calibration ratio between a reference blood glucose measurement value and its corresponding uncalibrated measurement value from the data management application 610 and/or the adaptive filtering module 714. In one or more embodiments, the expected calibration factor may be a fixed value that is empirically determined by testing multiple sensing elements 604 and/or sensing arrangements 600 and determining a nominal (or average) calibration ratio across the tested sensing elements 604 and/or sensing arrangements 600. For example, in one embodiment, the expected calibration factor is a fixed value equal to 5 mg/dL/nA. In other embodiments, the calibration application 612 may dynamically determine the expected calibration factor as a historical average of the raw calibration factor values determined during previous iterations of the calibration factor determination process 1300 with preceding blood glucose-current measurement pairs. In exemplary embodiments, the range of acceptable values is chosen to encompass the expected calibration factor. For example, in one embodiment, the acceptable range of values is chosen to be from the expected calibration factor minus a threshold amount to the expected calibration factor plus the threshold amount, such that any raw calibration factor within that range (e.g., the expected calibration factor value plus/minus the threshold amount) would be adjusted.

In exemplary embodiments, the calibration application 612 determines the adjusted calibration factor ($CF_{ADJ}$) as a weighted sum of the expected calibration factor ($CF_{EXP}$) and the raw calibration factor using the equation $CF_{ADJ} = \gamma CF_{EXP} + (1-\gamma) CF_R$, where $\gamma$ represents the weighting factor obtained for the expected calibration factor. In one embodiment, the weighting factor for the expected calibration factor has a fixed value between zero and one (e.g., a fixed percentage). In other embodiments, the calibration application 612 may dynamically determine the expected calibration factor weighting factor based on one or more factors. For example, if the expected calibration factor is determined based on a number of raw calibration factor values determined during previous iterations of the calibration factor determination process 1300, the expected calibration factor weighting factor may increase as the number of raw calibration factor values used to determine the expected calibration factor, and vice versa, thereby reflecting the relative confidence or reliability associated with the expected calibration factor. After the calibration application 612 determines the adjusted calibration factor, the calibration application 612 may transmit or otherwise provide the adjusted calibration factor to the pump control system 520 via the communications interface 606 for use by the pump control system 520 to convert filtered current measurements provided by the data management application 610 and/or the adaptive filtering module 714 into sensed glucose measurement values (e.g., $SG = CF_{ADJ} \times i_{out}$) and subsequently generating delivery commands and/or graphical user interface displays using the sensed glucose measurement values. Additionally, the adjusted calibration factor may be provided to the data management application 610 and/or the signal analysis module 710 for determining the frequency and noise metrics for the filtered measurement signal as described above in the context of FIG. 9.

Still referring to FIG. 13, in exemplary embodiments, when the calibration factor determination process 1300 determines that the raw calibration factor is not within an acceptable range of values, the calibration factor determination process 1300 proceeds by identifying or otherwise determining whether the blood glucose-current measurement pair was obtained during a startup period where the sensitivity of the sensing arrangement is abnormal or otherwise deviates from its likely long-term sensitivity (task 1316). In this regard, in some situations, the sensitivity of the sensing element 604 may initially be abnormally high or abnormally low upon initialization of the sensing element 604 before settling or otherwise converging towards a sensitivity that would result in a raw calibration factor value within the acceptable range of values for the raw calibration factor. In exemplary embodiments, when the calibration factor determination process 1300 determines the calibration attempt was performed during a startup period for the sensing arrangement, the calibration factor determination process 1300 continues by dynamically adjusting the calibration factor towards an expected calibration factor (task 1320). As described in greater detail below in the context of FIG. 14, the calibration application 612 determines an adjusted calibration factor based at least in part on the raw calibration factor in a manner that results in the adjusted calibration factor converging towards an expected calibration factor value or an acceptable range of values for the calibration factor. In this regard, as the amount of time elapsed since the calibration attempt increases, the difference between the adjusted calibration factor and the expected calibration factor (or alternatively, the acceptable range of values for the calibration factor) decreases.

Figure 14:
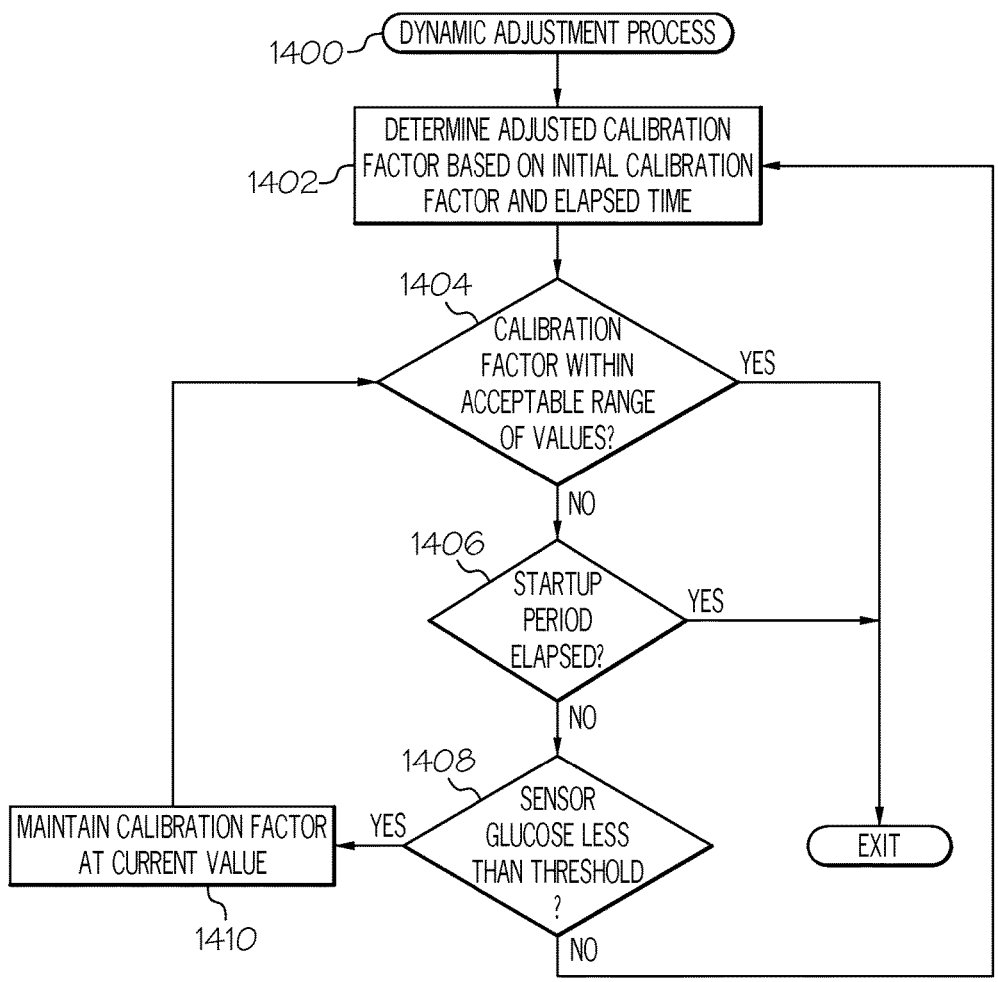
FIG. 14 is a flow diagram of an exemplary dynamic adjustment process suitable for implementation in conjunction with the calibration factor determination process of FIG. 13.

Referring now to FIG. 14, in one or more embodiments, the calibration application 612 performs a dynamic calibration factor adjustment process 1400 to dynamically adjust the calibration factor towards an expected calibration factor value (or a range of values) when the calibration attempt is performed during a startup period for the sensing element 604 of the sensing arrangement 504, 600. The dynamic adjustment process 1400 begins by calculating or otherwise determining an adjusted calibration factor based on the raw calibration factor and the amount of time that has elapsed since the calibration attempt (task 1402). In one embodiment, the calibration application 612 calculates the adjusted calibration factor using the equation $CF_{ADJ}=CF_R+t(p_1 CF_R+p_2)$, where t is the amount of time elapsed since the time associated with the raw calibration factor and $p_1$ and $p_2$ are scalar values configured to linearly adjust the adjusted calibration factor towards the expected calibration factor.

The illustrated process 1400 continues by identifying or otherwise determining whether the calibration factor is within an acceptable range of values (task 1404) and automatically terminating the dynamic adjustment process 1400 when the calibration factor is within the acceptable range of values. In this regard, the calibration application 612 ceases adjusting the calibration factor once the amount of time that has elapsed since the calibration attempt has resulted in an adjusted calibration factor that is sufficiently close to the expected calibration factor. In one or more embodiments, the calibration application 612 stops adjusting the calibration factor when the adjusted calibration factor is within a range of acceptable calibration factor values, where the range encompasses the expected calibration factor. In some embodiments, the calibration application 612 also confirms that the raw calibration factor does not exceed a maximum calibration factor value or fall below a minimum calibration factor value. For example, in one embodiment, the calibration application 612 only allows the calibration factor to be adjusted when the raw calibration factor is within the range of the minimum calibration factor value to the lower end of the range of acceptable calibration factor values or within the range of the upper end of the range of acceptable calibration factor values to the maximum calibration factor value. The dynamic adjustment process 1400 exits and provides indication that recalibration is required (e.g., task 1322) when the raw calibration factor is less than the minimum calibration factor value or greater than the maximum calibration factor value.

Still referring to FIG. 14, the dynamic adjustment process 1400 continues by verifying or otherwise confirming that the amount of time that has elapsed since the sensing element 604 of the sensing arrangement 504, 600 was initialized is less than the startup period for the sensing element 604 (task 1406). In this regard, the calibration application 612 or another component of the control module 602 may implement a timer or another similar feature to track or otherwise monitor the amount of time elapsed since the sensing element 604 was installed, replaced, or otherwise initialized, and terminate the dynamic adjustment process 1400 when the calibration application 612 detects that the elapsed time is greater than a threshold startup time period. For example, in one embodiment, the threshold startup time period is set to ten hours, such that the calibration application 612 automatically terminates the dynamic adjustment process 1400 when ten hours have elapsed since the sensing element 604 was first installed in the sensing arrangement 504, 600.

The illustrated process 1400 continues by identifying or otherwise determining whether the sensed glucose value corresponding to the most recent uncalibrated filtered current measurement value and the adjusted calibration factor value is less than a threshold amount (task 1408). In this regard, the calibration application 612 multiplies the most recently obtained uncalibrated filtered current measurement value from the data management application 610 and/or the adaptive filtering module 714 by the current adjusted calibration factor to determine the current sensed glucose value (e.g., $SG=CF_{ADJ} \times i_{out}$). The dynamic adjustment process 1400 automatically suspends adjusting the calibration factor when the sensed glucose value is less than a threshold glucose concentration and maintains the calibration factor at its current value (task 1410). For example, in one embodiment, the monitoring application 614 automatically maintains the current calibration factor value when the current sensed glucose value is less than 60 mg/dL. In this regard, the dynamic adjustment process 1400 does not adjust the calibration factor when the sensed glucose value is indicative of a potential hypoglycemic condition of the user. As illustrated in FIG. 14, the dynamic adjustment process 1400 may repeat until the adjusted calibration factor is within an acceptable range of calibration factor values or the sensor startup period has elapsed (e.g., a threshold number of hours from initialization of the sensing element 604).

Referring again to FIG. 13, in the illustrated embodiment, when the calibration factor determination process 1300 determines that the raw calibration factor is not within an acceptable range of values and that the sensor startup period has elapsed, the calibration factor determination process 1300 identifies or otherwise determines whether the blood glucose-current measurement pair was obtained at a point in time when the output from the sensing element was abnormally low (task 1318), and if so, the calibration factor determination process 1300 dynamically adjusts the calibration factor towards an expected calibration factor (task 1320). In exemplary embodiments, the calibration application 612 detects that the uncalibrated filtered current measurement value paired with the new blood glucose reference measurement value is abnormally low when the calibration ratio for the new blood glucose reference measurement value and its paired uncalibrated filtered current measurement value is greater than the calibration factor currently being utilized (e.g., the calibration factor determined by the calibration factor determination process 1300 on the preceding calibration attempt) by at least a threshold amount, the uncalibrated filtered current measurement value is less than a threshold current, and the current calibration factor is less than a threshold calibration value. For example, in one embodiment, the calibration application 612 detects the low current calibration condition when the calibration ratio is more than a threshold percentage greater than the current calibration factor, the uncalibrated filtered current measurement value is less than threshold current value, and the current calibration factor is less than a threshold calibration factor. Depending on the embodiment, after detecting the low current calibration condition, the calibration application 612 may fail to update the calibration buffer to include the current blood glucose-current measurement pair (e.g., by failing to evict the oldest blood glucose-current measurement pair from the buffer), or alternatively, the calibration application 612 may flag the current blood glucose-current measurement pair for eviction/replacement on the next calibration attempt if the calibration ratio associated with the next blood glucose-current measurement pair is less than the calibration ratio associated with the current blood glucose-current measurement pair.

In exemplary embodiments, after detecting the low current calibration condition, the calibration application 612 utilizes the raw calibration factor until identifying that the sensing element 604 has recovered from the low current condition, and thereafter, automatically begins dynamically adjusting the raw calibration factor for the new blood glucose-current measurement pair in response to detecting the recovery. In one embodiment, the calibration application 612 detects recovery from the low current condition when the uncalibrated measurement value from the data management application 610 and/or the adaptive filtering module 714 exceeds the uncalibrated measurement value of the blood glucose-current measurement pair by at least a threshold percentage of the paired uncalibrated measurement value. In a similar manner as described above, the calibration application 612 may linearly adjust the calibration factor towards the expected calibration factor (e.g., 5 mg/dL/nA) as the amount of time elapsed increases until the adjusted calibration factor is less than a threshold amount or the adjusted calibration factor is within a threshold percentage of the preceding calibration factor. Additionally, in one or more embodiments, the calibration application 612 stops adjusting the calibration factor in response to a new (or subsequent) calibration attempt having a calibration ratio that is not more than the threshold percentage greater than the current calibration factor. It should be noted that in such embodiments, the calibration factor determination process 1300 will be performed using the subsequent blood glucose-current measurement pair to determine a new calibration factor for use in converting subsequent current measurements into sensed glucose values.

Referring again to FIG. 13, when the calibration factor determination process 1300 determines that the raw calibration factor is not within an acceptable range of values, and that that deviation is not attributable to the sensor startup period or an abnormally low current measurement, the calibration factor determination process 1300 automatically generates or otherwise provides a notification to the user that indicates recalibration is required (task 1322). For example, the calibration application 612 may transmit or otherwise provide a notification to the pump control system 520 that indicates the calibration was unsuccessful, and in response, the pump control system 520 may generate or otherwise provide one or more auditory and/or visual notifications to the user via one or more output user interface element(s) 540 that a new blood glucose measurement value is required in a similar manner as described above (e.g., task 1212).

Figure 15:
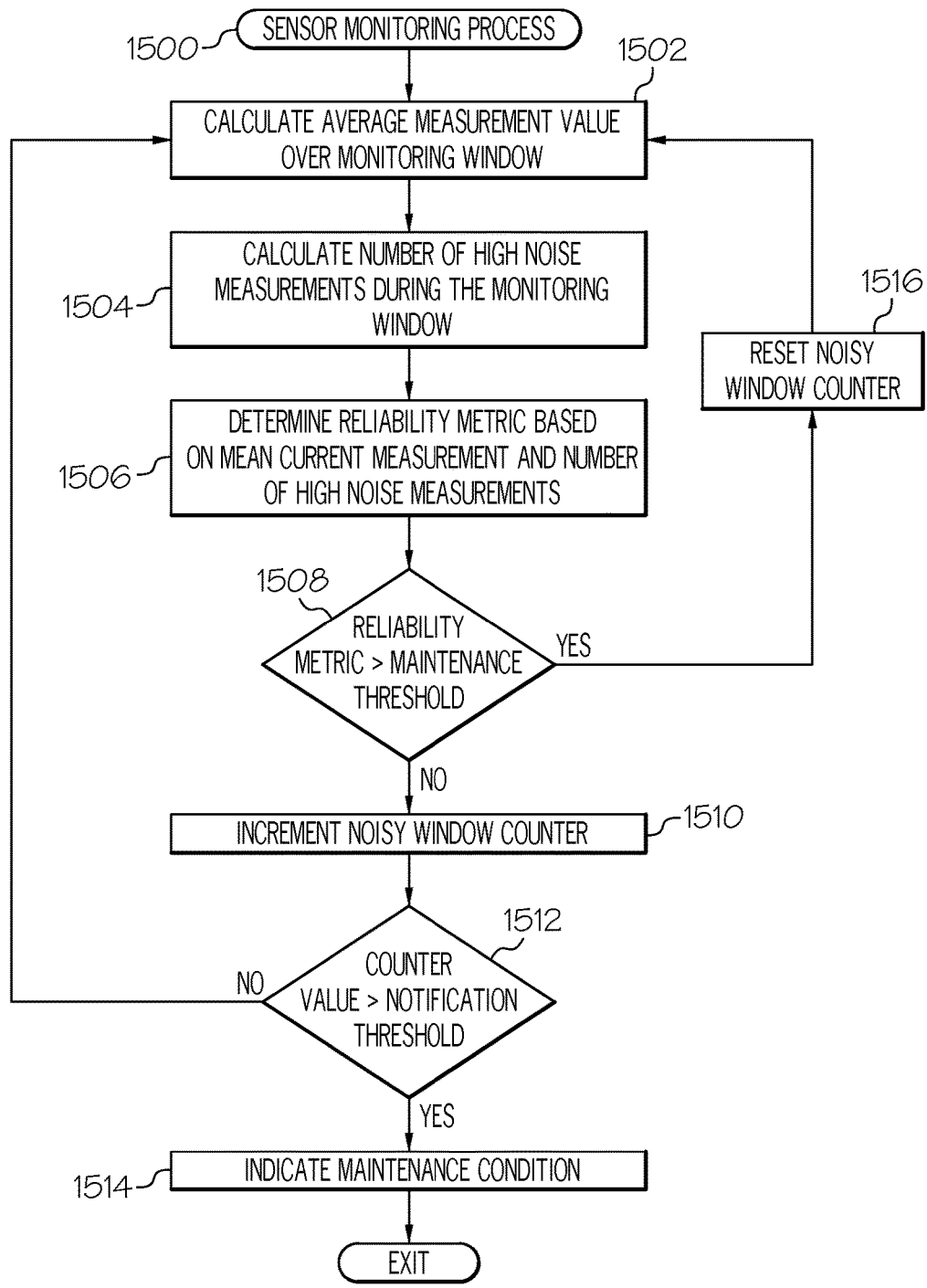
FIG. 15 is a flow diagram of an exemplary sensor monitoring process suitable for implementation by the health monitoring application in the sensing arrangement of FIG. 6.

FIG. 15 depicts an exemplary sensor monitoring process 1500 for identifying when a maintenance condition exists for a sensing element. In this regard, a maintenance condition indicates that the sensing element should be replaced or that some other maintenance of the sensing element should otherwise be performed (e.g., inspecting electrical connectivity to/from the sensing element, ensuring the sensing element is properly inserted and/or fitted in a housing of a sensing device, or the like). The various tasks performed in connection with the sensor monitoring process 1500 may be performed by hardware, firmware, software executed by processing circuitry, or any combination thereof. For illustrative purposes, the following description refers to elements mentioned above in connection with FIGS. 1-7. In practice, portions of the sensor monitoring process 1500 may be performed by different elements of the sensing arrangement 504, 600 and/or the control system 500. That said, in exemplary embodiments described herein, the sensor monitoring process 1500 is performed by the health monitoring application 614 implemented by the control module 602 to detect when the sensing element 604 should be replaced. It should be appreciated that the sensor monitoring process 1500 may include any number of additional or alternative tasks, the tasks need not be performed in the illustrated order and/or the tasks may be performed concurrently, and/or the sensor monitoring process 1500 may be incorporated into a more comprehensive procedure or process having additional functionality not described in detail herein. Moreover, one or more of the tasks shown and described in the context of FIG. 15 could be omitted from a practical embodiment of the sensor monitoring process 1500 as long as the intended overall functionality remains intact.

The illustrated sensor monitoring process 1500 calculates or otherwise determines an average filtered current measurement value over the duration of a particular monitoring window (task 1502). In this regard, the monitoring application 614 receives or otherwise obtains the uncalibrated filtered current measurements output by the data management application 610 and/or the adaptive filtering module 714 and averages any filtered current measurements occurring within a particular monitoring window of time. For example, in one embodiment, the monitoring application 614 implements a monitoring period of two hours, where the monitoring application 614 calculates the mean current measurement for a respective monitoring period by averaging the filtered current measurements output by the data management application 610 and/or the adaptive filtering module 714 over a consecutive two hour time period (e.g., 24 consecutive samples when filtered measurements are obtained every 5 minutes).

In exemplary embodiments, the sensor monitoring process 1500 also calculates or otherwise determines a number of filtered current measurement values during the particular monitoring window that have an associated noise metric greater than a threshold value (task 1504). In this regard, the monitoring application 614 implements a counter or another similar feature to track the number of filtered current measurements having an associated noise metric (e.g., the estimated signal noise metric determined by the signal analysis module 710) that exceeds a threshold value. In one embodiment where the signal analysis module 710 determines an estimated signal noise metric by scaling the second derivative metric by the calibration factor and clips the noise metric to an upper limit as described above, the monitoring application 614 identifies a high noise measurement when the noise metric associated with a filtered measurement is greater than a fraction of the upper limit (e.g., a percentage or fraction of the upper limit) and increments the counter associated with the high noise measurements. For example, if the signal analysis module 710 clips the estimated signal noise to a maximum value, the monitoring application 614 may identify a high noise measurement when the noise metric associated with a filtered measurement is greater than eighty percent of the maximum value. It should be noted that in some embodiments, an adjusted calibration factor may be used when determining the estimated signal noise metric, that is, the dynamic adjustment process 1400 may be performed concurrently to the sensor monitoring process 1500.

After determining the average measurement value over a monitoring window and a number of high noise measurements during that monitoring window, the sensor monitoring process 1500 continues by calculating or otherwise determining a sensor reliability metric based on relationship between the average measurement value and the number of high noise measurements (task 1506). In exemplary embodiments, the monitoring application 614 determines a sensor reliability metric as a ratio of the average measurement value to the number of high noise measurements, for example, by dividing the average current measurement value for the monitoring window by the number of high noise measurements for the monitoring window (plus one, if desired, to prevent divide by zero). In this regard, the sensor reliability metric calculation accounts for the anticipated relationship between the measurement signal level and the magnitude of the fluctuations in the measurement signal (e.g., larger signal fluctuations at higher signal levels are more likely to lead to more measurements classified as high noise and vice versa).

After determining a sensor reliability metric, the sensor monitoring process 1500 continues by determining whether the sensor reliability metric is greater than a maintenance threshold that is indicative of a healthy sensing element (task 1508). In this regard, a higher value for the sensor reliability metric indicates a lower number of high noise measurements relative to the measurement signal level over the monitoring period, while a lower value for the sensor reliability metric indicates a higher number of high noise measurements relative to the measurement signal level over the monitoring period. Thus, when the sensor reliability metric is less than the maintenance threshold, the sensor monitoring process 1500 identifies or otherwise classifies the monitoring window as a high noise monitoring window and increments or otherwise increases a count of the number of consecutive high noise monitoring windows and determines whether the number of consecutive high noise monitoring windows exceeds a notification threshold amount (tasks 1510, 1512). For example, in one embodiment, the notification threshold amount is chosen to be equal to three, such that the monitoring application 614 determines that the user should be notified of the maintenance condition with respect to the sensing element 604 when the filtered measurement values exhibit relatively high noise over at least six consecutive hours (e.g., 3 consecutive monitoring windows with a low sensor reliability metric). In this manner, when the filtered measurement values exhibit relatively high noise for a consecutive duration of time that exceeds a threshold amount of time, the sensor monitoring process 1500 determines that the maintenance notification criteria have been satisfied and generates or otherwise provides a user notification that indicates maintenance condition exists with respect to the sensing element (task 1514). For example, in one embodiment, the monitoring application 614 may operate an output user interface 606 to indicate replacement of the sensing element 604 should be performed. In other embodiments, the monitoring application 614 may instruct the pump control system 520 to notify the user of the maintenance condition via a user interface 540 associated with the infusion device 502. Alternatively, when the sensor reliability metric for a monitoring window is greater than the maintenance threshold and indicative of a healthy sensing element, the sensor monitoring process 1500 resets or otherwise reinitializes the number of consecutive high noise monitoring windows (task 1516).

It should be noted that in one or more exemplary embodiments, the sensor monitoring process 1500 is not performed immediately upon initialization of a sensing element. For example, in one or more embodiments, the monitoring application 614 may implement a timer or another similar feature to track the amount of time elapsed since the sensing element 604 was installed or initialized in the sensing arrangement 600 and begin performing the sensor monitoring process 1500 only after the elapsed time is greater than a threshold amount of time. In this regard, the sensor monitoring process 1500 may not performed during the initialization period when the output signals from the sensing element 604 are unstable (e.g., tasks 1202, 1204) or the sensor startup period where the output signals from the sensing element 604 may otherwise be unsettled or unreliable (e.g., task 1316). For example, in one embodiment, the monitoring application 614 does not perform the sensor monitoring process 1500 until at least 24 hours have elapsed since the sensing element 604 was installed or initialized.

For the sake of brevity, conventional techniques related to glucose sensing and/or monitoring, closed-loop glucose control, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of providing indication when replacement of an interstitial glucose sensing element of a sensing arrangement should be performed in connection with operating an infusion device operable to deliver fluid to a user based on measurements indicative of an interstitial fluid glucose level of the user provided by the sensing arrangement, the fluid influencing the physiological condition of the user, the method comprising:

obtaining, by a control module coupled to the interstitial glucose sensing element of the sensing arrangement, a plurality of uncalibrated measurements corresponding to a monitoring period based on output signals provided by the sensing element, wherein the output signals are influenced by the interstitial fluid glucose level of the user;

obtaining, by the control module, a calibration factor for converting the plurality of uncalibrated measurements to a plurality of calibrated measurement values for the physiological condition;

for each respective measurement of the plurality of uncalibrated measurements:

determining a second derivative metric associated with the respective measurement based at least in part on a difference between a first derivative metric associated with the respective measurement and the first derivative metric associated with the preceding measurement of the plurality of uncalibrated measurements, wherein the second derivative metric associated with a most recent measurement of the plurality of uncalibrated measurements comprises the greater of a difference between the first derivative metric associated with the most recent measurement and the first derivative metric associated with the immediately preceding measurement of the plurality of uncalibrated measurements and an average magnitude of second derivative metric values associated with the plurality of uncalibrated measurements; and
scaling the second derivative metric associated with the respective measurement by the calibration factor to determine a noise metric for the respective measurement of the plurality of uncalibrated measurements;
determining, by the control module, a number of high noise measurements for the monitoring period based on the noise metrics for the respective measurements of the plurality of uncalibrated measurements;
determining, by the control module, an output measurement value indicative of the interstitial fluid glucose level based at least in part on the most recent measurement of the plurality of uncalibrated measurements and at least one of the first derivative metric associated with the most recent measurement and the second derivative metric associated with the most recent measurement;
transmitting, by a communications interface coupled to the control module, the output measurement value to the infusion device, wherein a delivery command for operating a motor of the infusion device to autonomously control delivery of the fluid to the user is determined based at least in part on the output measurement value and the calibration factor; and
providing, via an output interface of the sensing arrangement, indication replacement of the interstitial glucose sensing element should be performed when a reliability metric influenced by the number of high noise measurements violates a first threshold.

2. The method of claim 1, further comprising determining a number of consecutive monitoring periods that violated the first threshold when the number of high noise measurements for the monitoring period violates the first threshold, wherein providing the indication comprises automatically providing the indication when the number of consecutive monitoring periods is greater than a second threshold.

3. The method of claim 1, further comprising: determining an average measurement value for the monitoring period based on the plurality of uncalibrated measurements; and
determining the reliability metric based at least in part on a ratio of the average measurement value to the number of high noise measurements.

4. The method of claim 3, further comprising determining a second number of consecutive monitoring periods that violated the first threshold when the reliability metric for the monitoring period violates the first threshold, wherein providing the indication comprises providing the indication when the second number of consecutive monitoring periods is greater than a second threshold.

5. The method of claim 1, wherein determining the number of high noise measurements comprises determining the number of respective measurements of the plurality of uncalibrated measurements having an associated noise metric greater than a threshold value.

6. The method of claim 5, further comprising determining a second number of consecutive monitoring periods that violated the first threshold when the reliability metric for the monitoring period violates the first threshold, wherein providing the indication comprises providing the indication when the second number of consecutive monitoring periods is greater than a second threshold.

7. A non-transitory computer-readable medium having computer-executable instructions stored thereon that, when executed by the control module, cause the control module to perform the method of claim 1.

8. The method of claim 1, further comprising:
periodically sampling the output signals of the interstitial glucose sensing element to obtain a plurality of unfiltered measurement values stored in an unfiltered sample buffer;
periodically obtaining a plurality of unfiltered measurement values from the unfiltered sample buffer;
applying a filter to the plurality of uncalibrated measurements to obtain a filtered measurement; and
storing the filtered measurement in a filtered sample buffer, wherein obtaining, the plurality of uncalibrated measurements corresponding to the monitoring period comprises obtaining the plurality of uncalibrated measurements from the filtered sample buffer.

9. The method of claim 1, wherein obtaining the plurality of uncalibrated measurements comprises obtaining a plurality of five-minute filtered measurement values.

10. The method of claim 9, further comprising:
periodically sampling the output signals of the interstitial glucose sensing element on a per-minute to obtain a plurality of unfiltered measurement values stored in an unfiltered sample buffer; and
periodically obtaining the plurality of unfiltered measurement values from the unfiltered sample buffer every five minutes;
applying a filter to the plurality of unfiltered measurement values obtained from the unfiltered sample buffer to obtain the respective five-minute filtered measurement values of the plurality of five-minute filtered measurement values.

11. The method of claim 10, wherein the first derivative metric associated with each respective measurement of the plurality of uncalibrated measurements comprises a difference between a respective five-minute filtered measurement value and an immediately preceding five-minute filtered measurement value.

12. The method of claim 11, further comprising:
converting the most recent measurement into a sensed glucose value using the calibration factor; and
determining the delivery command for operating the motor of the infusion device to deliver the fluid to the user based at least in part on the sensed glucose value.

13. The method of claim 1, wherein determining the delivery command comprises:
converting the most recent measurement into a sensed glucose value using the calibration factor; and
determining an insulin dosage command based at least in part on a difference between the sensed glucose value and a target glucose value.

14. The method of claim 13, further comprising operating the motor of the infusion device to achieve the insulin dosage command.

15. An infusion system providing indication when replacement of an interstitial glucose sensing element should be performed, the interstitial glucose sensing element providing output signals influenced by an interstitial fluid glucose level in a body of a user, the infusion system comprising:
a communications interface; and
a control module coupled to the interstitial glucose sensing element and the communications interface to determine a plurality of uncalibrated filtered measurements based on the output signals, determine one or more noise metrics associated with a subset of the plurality of uncalibrated filtered measurements corresponding to a monitoring period based at least in part on a calibration factor for converting the plurality of uncalibrated filtered measurements to a plurality of calibrated measurement values for the physiological condition, determine a reliability metric for the monitoring period based on the one or more noise metrics, determine an output measurement value indicative of the interstitial fluid glucose level based at least in part on a most recent measurement of the subset and at least one of a first derivative metric associated with the most recent measurement and a second derivative metric associated with the most recent measurement, transmit the output measurement value to an infusion device via the communications interface, and provide indication for replacement of the sensing element when the reliability metric violates a first threshold, wherein:
- a delivery command for operating a motor of the infusion device to autonomously control delivery of a fluid influencing the interstitial fluid glucose level to the user is determined based at least in part on the output measurement value and the calibration factor;
- the one or more noise metrics comprise a respective noise metric for each respective uncalibrated filtered measurement of the subset and an average measurement value of the subset of the plurality of uncalibrated filtered measurements for the monitoring period;
- the respective noise metric for each respective uncalibrated filtered measurement comprises a second derivative metric associated with the respective uncalibrated filtered measurement scaled by the calibration factor;
- the second derivative metric associated with the most recent measurement of the subset comprises the greater of a difference between the first derivative metric associated with the most recent measurement and the first derivative metric associated with an immediately preceding measurement of the subset and an average magnitude of the second derivative metric values associated with the subset;
- the reliability metric comprises a ratio of the average measurement value to a number of high noise measurements over the monitoring period; and
- the number of high noise measurements comprises a number of filtered measurements of the subset having respective noise metrics that violate a second threshold.

16. The infusion system of claim 15, further comprising an output user interface element coupled to the control module, wherein providing the indication comprises the control module generating a user notification indicating replacement of the sensing element when the reliability metric violates the first threshold.

17. The infusion system of claim 15, wherein the control module determines a second number of consecutive monitoring periods that violated the first threshold when the reliability metric for the monitoring period violates the first threshold and automatically provides the indication when the second number of consecutive monitoring periods is greater than a third threshold.

18. A method of providing indication when replacement of an interstitial glucose sensing element should be performed in connection with operating an infusion device operable to deliver insulin to a body of a user, the method comprising:
- determining, by a control module coupled to the interstitial glucose sensing element, a plurality of uncalibrated filtered measurements indicative of an interstitial fluid glucose level in the body of the user based on output signals from the interstitial glucose sensing element, wherein the output signals are influenced by the interstitial fluid glucose level in the body;
- obtaining, by the control module, a calibration factor for converting the plurality of uncalibrated filtered measurements to a plurality of calibrated sensor glucose values;
- for each respective filtered measurement of the subset:
  - determining a second derivative metric associated with the respective filtered measurement of the subset based at least in part on a difference between a first derivative metric associated with the respective filtered measurement and the first derivative metric associated with the preceding filtered measurement of the subset, wherein the second derivative metric associated with a most recent filtered measurement of the subset comprises the greater of a difference between the first derivative metric associated with the most recent filtered measurement and the first derivative metric associated with the immediately preceding filtered measurement of the subset and an average magnitude of second derivative metric values associated with the subset;
  - scaling the second derivative metric associated with the respective filtered measurement by the calibration factor to determine a respective noise metric associated with the respective filtered measurement of the subset;
- determining, by the control module, a number of high noise measurements during the monitoring period as a number of respective filtered measurements of the subset having an associated noise metric greater than a threshold value;
- determining, by the control module, a reliability metric for the monitoring period as a ratio of an average measurement value for the monitoring period to the number of high noise measurements during the monitoring period;
- determining, by the control module, an output measurement value indicative of the interstitial fluid glucose level based at least in part on the most recent measurement of the subset and at least one of the first derivative metric associated with the most recent measurement and the second derivative metric associated with the most recent measurement;
- transmitting, by a communications interface coupled to the control module, the output measurement value to the infusion device, wherein a delivery command for operating a motor of the infusion device to autonomously control delivery of the fluid to the user is determined based at least in part on the output measurement value and the calibration factor; and
- providing, via an output interface, a user notification to replace the interstitial glucose sensing element when the reliability metric violates a first threshold.

19. The method of claim 18, further comprising determining a second number of consecutive monitoring periods having an associated reliability metric less than the first threshold when the reliability metric for the monitoring period is less than the first threshold, wherein providing the user notification comprises automatically providing the user notification when the second number of consecutive monitoring periods is greater than a second threshold.

* * * * *